US010920249B2

(12) United States Patent
Subhas et al.

(10) Patent No.: US 10,920,249 B2
(45) Date of Patent: *Feb. 16, 2021

(54) METHOD AND APPARATUS FOR CO2 SEQUESTRATION

(71) Applicants: California Institute of Technology, Pasadena, CA (US); University of Southern California, Los Angeles, CA (US); Yissum Research Development Company of the Hebrew University of Jerusalem Ltd., Jerusalem (IL)

(72) Inventors: Adam Vinay Subhas, Los Angeles, CA (US); William Max Berelson, Los Angeles, CA (US); Nick Everett Rollins, Santa Monica, CA (US); Jess Firey Adkins, Altadena, CA (US); Jonathan Erez, Jerusalem (IL)

(73) Assignees: California Institute of Technology, Pasadena, CA (US); University of Southern California, Los Angeles, CA (US); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 330 days.

This patent is subject to a terminal disclaimer.

(21) Appl. No.: 15/996,121

(22) Filed: Jun. 1, 2018

(65) Prior Publication Data

US 2018/0371506 A1   Dec. 27, 2018

Related U.S. Application Data

(63) Continuation of application No. 14/975,584, filed on Dec. 18, 2015, now Pat. No. 9,988,653.

(Continued)

(51) Int. Cl.
*B01D 53/34*  (2006.01)
*B01D 53/62*  (2006.01)
(Continued)

(52) U.S. Cl.
CPC .............. *C12P 7/40* (2013.01); *B01D 53/346* (2013.01); *B01D 53/62* (2013.01); *B01D 53/77* (2013.01);
(Continued)

(58) Field of Classification Search
CPC .......... B01D 2251/606; B01D 2251/90; B01D 2255/804; B01D 53/346; B01D 53/62;
(Continued)

(56) References Cited

U.S. PATENT DOCUMENTS 7,655,193 B1   2/2010   Rau et al.
8,329,459 B2   12/2012  Parent et al.
(Continued)

FOREIGN PATENT DOCUMENTS

CN   101810985 A   8/2010
CN   101918110 A   12/2010
(Continued)

OTHER PUBLICATIONS

International Preliminary Report on Patentability for International Application PCT/US2015/066920, Report dated Jun. 20, 2017, dated Jun. 29, 2017, 8 Pgs.
(Continued)

*Primary Examiner* — Cabrena Holecek
(74) *Attorney, Agent, or Firm* — KPPB LLP

(57) ABSTRACT

Processes, methods, and apparatus for carbon sequestration utilizing catalysis schemes configured to provide high concentrations of hydrated $CO_2$ in proximity with a sequestration agent are provided. Reactants are combined with catalyst such that at least two regions of controlled catalytic
(Continued)

activity form encompassing at least the interface between a sequestration agent and an aqueous solution containing dissolved $CO_2$. Suitable reactants include various sequestration agents, catalyst, and carbon dioxide dissolved in an aqueous solution (seawater, for example). Possible products include bicarbonate and metal cations.

20 Claims, 16 Drawing Sheets

Related U.S. Application Data

(60) Provisional application No. 62/208,356, filed on Aug. 21, 2015, provisional application No. 62/093,958, filed on Dec. 18, 2014.

(51) Int. Cl.
*B01D 53/77* (2006.01)
*B01D 53/86* (2006.01)
*C12M 1/00* (2006.01)
*C12M 1/02* (2006.01)
*C12P 7/40* (2006.01)

(52) U.S. Cl.
CPC ......... *B01D 53/8671* (2013.01); *C12M 23/58* (2013.01); *C12M 27/00* (2013.01); *C12M 29/00* (2013.01); *C12M 29/04* (2013.01); *C12M 29/18* (2013.01); *B01D 2251/606* (2013.01); *B01D 2251/90* (2013.01); *B01D 2255/804* (2013.01); *Y02C 20/40* (2020.08); *Y02P 20/151* (2015.11); *Y02P 20/59* (2015.11)

(58) Field of Classification Search
CPC .... B01D 53/77; B01D 53/8671; C12M 23/58; C12M 27/00; C12M 29/00; C12M 29/04; C12M 29/18; C12P 7/40; Y02C 10/04; Y02P 20/152; Y02P 20/59
See application file for complete search history.

(56) References Cited

U.S. PATENT DOCUMENTS

| | | | |
|---|---|---|---|
| 8,722,391 B2 | 5/2014 | Fradette et al. | |
| 8,895,280 B2 * | 11/2014 | Rambo | C12Y 402/01001 435/182 |
| 9,988,653 B2 | 6/2018 | Subhas et al. | |
| 2001/0022952 A1 | 9/2001 | Rau et al. | |
| 2011/0070137 A1 | 3/2011 | Brock et al. | |
| 2013/0171720 A1 | 7/2013 | McKenna et al. | |
| 2013/0319230 A1 | 12/2013 | Patel | |
| 2016/0177344 A1 | 6/2016 | Subhas et al. | |

FOREIGN PATENT DOCUMENTS

| | | |
|---|---|---|
| CN | 102105569 A | 6/2011 |
| CN | 102343199 A | 2/2012 |
| CN | 102612549 A | 7/2012 |
| CN | 106076066 A | 11/2016 |
| CN | 108377650 A | 8/2018 |
| CN | 110079435 A | 8/2019 |
| WO | 2008115662 A2 | 9/2008 |
| WO | 2014000113 A1 | 1/2014 |
| WO | 2016100937 | 6/2016 |

OTHER PUBLICATIONS

International Search Report and Written Opinion for International Application No. PCT/US2015/066920, Search completed Apr. 8, 2016, dated Apr. 8, 2016, 10 Pgs.

Anbeek, "Surface roughness of minerals and implications for dissolution studies", Geochimica et Cosmochimica Acta, Jan. 23, 1992, vol. 56, pp. 1461-1469.

Andersson et al., "Net Loss of CaCO3 from a subtropical calcifying community due to seawater acidification: mesocosm-scale experimental evidence", Biogeosciences, Aug. 27, 2009, vol. 6, pp. 1811-1823.

Andersson et al., "Ocean Acidification and Coral Reefs: Effects on Breakdown, Dissolution, and Net Ecosystem Calcification", Annual Review of Marine Science, 2013, vol. 5, pp. 321-348.

Arakaki et al., "A Continuous and Mechanistic Representation of Calcite Reaction-Controlled Kinetics in Dilute Solutions at 25 Degrees C and 1 Atm Total Pressure", Aquatic Geochemistry, Jan. 20, 1995, vol. 1, pp. 105-130.

Archer et al., "Dynamics of fossil fuel CO2 neutralization by marine CaCO3", Global Biogeochemical Cycles, Jun. 1998, vol. 12, No. 2, pp. 259-276.

Bednarsek et al., "Limacina helicina shell dissolution as an indicate of declining habitat suitability owning to ocean acidification in the California current Ecosystem", Proceedings of the Royal Society B: Biological Sciences, Apr. 2, 2014, vol. 281, Jan. 23, 2014, 8 pgs.

Berelson et al., "Relating estimates of CaCO3 production, export, and dissolution in the water column To measurements of CaCO3 rain into sediment traps and dissolution of the sea floor: A revised global carbonate budget", Global Biogeochemical Cycles, Mar. 24, 2007, vol. 21, GB1024, 15 pgs.

Berger, "Foraminiferal Ooze: Solution at Depths", Science, Apr. 21, 1967, vol. 156, pp. 383-385.

Berner et al., "Dissolution Kinetics of Calcium Carbonate in Sea Water", American Journal of Science, Feb. 1974, vol. 274, pp. 108-134.

Boudreau, "Carbonate dissolution rates at the deep ocean floor", Geophysical Research Letters, Feb. 27, 2013, vol. 40, pp. 744-748.

Boudreau et al., "Ongoing transients in carbonate compensation", Global Biogeochemical Cycles, Nov. 4, 2010, vol. 24, GB4010, 13 pgs.

Brunauer et al., "Adsorption of Gases in Multimolecular Layers", Journal of the American Chemical Society, Feb. 1938, vol. 60, pp. 309-319.

Coto et al., "Fluid Phase Equilibria", vol. 324, Mar. 23, 2012, pp. 1-7.

Cubillas et al., "Experimental determination of the dissolution rates of calcite, aragonite, and bivalves", Chemical Geology, 2005, vol. 216, pp. 59-77.

De Kanel et al., "A simple technique for surface area determination", Journal of Physics E: Scientific Instruments, 1979, vol. 12, pp. 272-273.

Dickson et al., "A comparison of the equilibrium constants for the dissociation of carbonic acid in seawater media", Deep-Sea Research, Apr. 8, 1987, vol. 34, No. 10, pp. 1733-1743.

Dickson et al., "Guide to best practices for ocean CO2 measurements", Pices Special Publication 3, Oct. 12, 2007, 175 pgs.

Emerson et al., "Carbon fluxes at the sediment-water interface of the deep-sea; calcium carbonate preservation", Journal of Marine Research, 1981, pp. 139-162.

Feely et al., "Decadal changes in the aragonite and calcite saturation state of the Pacific Ocean", Global Biogeochemical Cycles, Jul. 4, 2012, vol. 26, GB3001, 15 pgs.

Finneran et al., "Calcite dissolution kinetics in saline waters", Chemical Geology, Aug. 7, 2009, vol. 268, pp. 137-146.

Fischer et al., "How predictable are dissolution rates of crystalline material?", Geochimica et Cosmochimica Acta, Sep. 19, 2012. vol. 98, pp. 177-185.

Fukuhara et al., "An in situ experiment of calcium carbonate dissolution in the central Pacific Ocean", International Journal of Greenhouse Gas Control, 2008, vol. 2, pp. 78-88.

Gehlen et al., "Reassessing the dissolution of marine carbonates: I Solubility", Deep-Sea Research I, Mar. 9, 2005, vol. 52, pp. 1445-1460.

Gehlen et al., "Reassessing the dissolution of marine carbonates: II Reaction kinetics", Deep-Sea Research I, Mar. 9, 2005, vol. 52, pp. 1461-1476.

(56) References Cited

OTHER PUBLICATIONS

Gledhill et al., "Calcite dissolution kinetics in Na—Ca—Mg—Cl brines", Geochimical et Cosmochimica Acta, Mar. 29, 2006, vol. 70, pp. 5802-5813.
Hales et al., "Evidence in support of first-order dissolution kinetics of calcite in seawater", Earth and Planetary Science Letters, Jan. 21, 1997, vol. 148, pp. 317-327.
Honjo et al., "Dissolution Rates of Calcium Carbonate in the Deep Ocean; An In-Situ Experiment in the North Atlantic Ocean", Earth and Planetary Science Letters, Mar. 9, 1978, vol. 40, pp. 287-300.
Ilyina et al., "Detection and projection of carbonate dissolution in water column and deep-sea sediments due to ocean acidification", Geophysical Research Letters, Mar. 30, 2012, vol. 39, L06606, 6 pgs.
Keir, "The dissolution kinetics of biogenic calcium carbonates in seawater", Geochimica et Cosmochimica Acta, 1980, vol. 44, pp. 241-252.
Leclercq et al., "$CO_2$ partial pressure controls the calcification rate of a coral community", Global Change Biology, 2000, vol. 6, pp. 329-334.
Macinnis et al., "The role of dislocations and surface morphology in calcite dissolution", Geochimica et Cosmochimica Acta, 1992, vol. 56, pp. 1113-1126.
Mehrbach et al., "Measurement of the Apparent Dissociation Constants of Carbonic Acid in Seawater at Atmospheric Pressure", Limnology and Oceanography, Nov. 1973, vol. 18, No. 6, pp. 897-907.
Milliman et al., "Biologically mediated dissolution of calcium carbonate above the chemical lysocline?", Deep-Sea Research I, Feb. 2, 1999, vol. 46, pp. 1653-1669.
Morse, "Dissolution Kinetics of Calcium Carbonate in Sea Water. III: A New Method for the Study of Carbonate Reaction Kinetics", American Journal of Science, Feb. 1974, vol. 274, pp. 97-107.
Morse et al., "The dissolution kinetics of major sedimentary carbonate materials", Earth-Science Reviews, 2002, vol. 58, pp. 51-84.
Mucci, "The Solubility of Calcite and Aragonite in Seawater at Various Salinities, Temperatures, and One Atmosphere Total Pressure", American Journal of Science, Sep. 1983, vol. 283, pp. 780-799.
Nickl et al., "Growth of Calcite Crystals in Gels", Journal of Electrochemical Society, 1969, vol. 116, No. 9, pp. 1258-1260.
Peterson, "Calcite: Rates of Dissolution in a Vertical Profile in the Central Pacific", Science, Dec. 23, 1996, vol. 154(3756), pp. 1542-1544.
Plummer et al., "The dissolution of calcite in $CO_2$-saturated solutions at 25 degrees C and 1 atmosphere total pressure", Geochimical et Cosmochimica Acta, 1976, vol. 40, pp. 191-202.
Rau, "$CO_2$ Mitigation via Capture and Chemical Conversion in Seawater", Environmental Science & Technology, Dec. 28, 2010, vol. 45, No. 3, pp. 1088-1092.
Sabine et al., "The Oceanic Sink for Anthropogenic $CO_2$", Science, Jul. 16, 2004, vol. 305, pp. 367-371.
Schwartz et al., "Growth of Vaterite and Calcite Crystals in Gels", Materials Research Bulletin, Oct. 5, 1971, vol. 6, pp. 1341-1344.
Shiraki et al., "Dissolution Kinetics of Calcite in 0.1 M NaCl Solution at Room Temperature: An Atomic Force Microscopic (AFM) Study", Aquatic Geochemistry, 2000, 6, pp. 87-108.
Sigman et al., "Glacial/interglacial variations in atmospheric carbon dioxide", Nature, Oct. 19, 2000, vol. 407, pp. 859-869.
Silverman et al., "Effect of aragonite saturation, temperature and nutrients on the community calcification rate of a coral reef", Journal of Geophysical Research, May 1, 2007, vol. 112, C05004, 14 pgs.
Sjoberg, "A fundamental equation for calcite dissolution kinetics", Geochimica et Cosmochimica Acta, 1976, vol. 40, pp. 441-447.
Sjoberg et al., "The Effect of Added Dissolved Calcium on Calcite Dissolution Kinetics in Aqueous Solutions at 25 degrees C", Chemical Geology, 1985, vol. 49, pp. 405-413.
Subhas et al., "A novel determination of calcite dissolution kinetics in seawater", Geochimica et Cosmochimica Acta, vol. 170, No. 1, Aug. 31, 2015, pp. 51-68.
Wang et al., "Comprehensive Study of the Hydration and Dehydration Reactions of Carbon Dioxide in Aqueous Solution", The Journal of Physical Chemistry A, 2010, vol. 114, pp. 1734-1740.
International Search Report and Written Opinion for International Application No. PCT/US2020/034300, Search completed Sep. 11, 2020, dated Sep. 11, 2020, 9 Pgs.

* cited by examiner

METHOD AND APPARATUS FOR CO2 SEQUESTRATION

RELATED APPLICATIONS

This application is a continuation of U.S. application Ser. No. 14/975,584 filed Dec. 18, 2015, which application claims priority to U.S. Provisional Patent Application No. 62/093,958 filed Dec. 18, 2014 and U.S. Provisional Patent Application No. 62/208,356 filed Aug. 21, 2015, the disclosures of which are incorporated herein by reference.

STATEMENT OF FEDERAL FUNDING

This invention was made with government support under 1220600 awarded by the National Science Foundation. The government has certain rights in the invention.

FIELD OF THE INVENTION

The present disclosure is directed to methods and apparatus for $CO_2$ sequestration.

BACKGROUND OF THE INVENTION

Carbon dioxide ($CO_2$) constitutes about 0.04% (400 parts per million) of the atmosphere. Despite its relatively small overall concentration, $CO_2$ is a potent greenhouse gas that plays an important role in regulating the Earth's surface temperature. Presently, anthropogenic $CO_2$ generation is taking place at a rate greater than it is being consumed and/or stored, leading to increasing concentrations of $CO_2$ in the atmosphere. There is a growing concern that rising levels of $CO_2$ in the earth's atmosphere may present a substantial environmental challenge. As a result, there is an increased interest in developing methods for removing $CO_2$ from emission streams and the atmosphere and storing it in a manner that prevents its future release into the atmosphere. This capture and storage is collectively known as $CO_2$ sequestration.

BRIEF SUMMARY OF THE INVENTION

The disclosure is generally directed to apparatus and methods for the capture and sequestration of $CO_2$ via a novel catalytic system.

Many embodiments are directed to a method for carbon dioxide sequestration including:
   dissolving carbon dioxide into an aqueous solution to form an aqueous carbon dioxide solution defined by a mineral undersaturation level;
   combining the aqueous carbon dioxide solution with a sequestration agent;
   titrating a hydrating catalyst into the aqueous carbon dioxide solution such that at least within a first catalysis region a mixture of catalyst and aqueous carbon dioxide solution is formed, said first catalysis region encompassing a second interfacial catalysis region located within the laminar boundary layer at the interface between the mixture and the carbonate sequestration agent; and
   reacting the aqueous carbon dioxide solution with the catalyst within the first catalysis region to produce protons in proximity to the second interfacial catalysis region such that the protons dissolve the sequestration agent;
   reacting the carbon dioxide within the aqueous carbon dioxide solution with the dissolved sequestration agent within the second interfacial catalysis region to produce an effluent comprising at least bicarbonate; and
   wherein within the second interfacial catalysis region the dissolution of the sequestration agent is enhanced such that the overall rate of dissolution of the sequestration agent within the catalytic region is higher than the rate of the uncatalyzed dissolution of the sequestration agent when exposed to an aqueous carbon dioxide solution having the same mineral undersaturation level.

In some other embodiments the sequestration agent is selected from the group consisting of a metal carbonate, or a silicate mineral.

In still other embodiments the sequestration agent is calcium carbonate and the catalyst is one of either carbonic anhydrase or a carbonic anhydrase analog.

In yet other embodiments the overall rate of dissolution of the carbonate sequestration agent is at least an order of magnitude higher than the rate of the uncatalyzed dissolution of the carbonate sequestration agent when exposed to an aqueous carbon dioxide solution having the same mineral undersaturation level.

In still yet other embodiments the mineral undersaturation level is held at less than 0.5.

In still yet other embodiments the method further includes placing at least the first catalysis region and the second interfacial catalysis region under a pressure of at least 500 psi such that the dissolution of the sequestration agent is increased relative to the unpressurized dissolution rate of the sequestration agent at the same mineral undersaturation.

In still yet other embodiments the method includes maintaining at least the second interfacial catalysis region at a temperature no greater than 200° C.

In still yet other embodiments further includes reacting with a condition agent the aqueous solution to reduce surface poisoning ions in the aqueous carbon dioxide solution.

In still yet other embodiments the aqueous solution has a circum-neutral pH.

In still yet other embodiments the aqueous solution is a brine solution.

In still yet other embodiments the aqueous carbon dioxide solution is combined in measured aliquots such that the mineral undersaturation level is maintained at a constant level.

In still yet other embodiments the method further includes stirring the aqueous solution within at least the first catalysis region such that a mixing zone forms wherein the aqueous carbon dioxide solution and catalyst intermingle and wherein the mixing zone is within the first catalysis region.

In still yet other embodiments the stirring forms a diffusion boundary layer around the second interfacial catalysis region the diffusion boundary defining a volume around the interfacial region of the sequestration agent on the order of 10 microns.

In still yet other embodiments the method further includes roughening the surface of the sequestration agent such that the grain size of the sequestration agent is no greater than 100 μm.

In still yet other embodiments the method further includes collecting and filtering the effluent from the reaction to capture at least one of catalyst or unreacted aqueous carbon dioxide solution, and reintroducing the catalyst and unreacted aqueous carbon dioxide solution into the first catalysis region.

In still yet other embodiments the catalyst operates to at least catalyze the protolysis of water in the aqueous solution and hydrate the $CO_2$ within the solution.

In still yet other embodiments the rate of dissolution is diffusion rate limited.

In still yet other embodiments at least one of either the pressure is increased or the temperature is decreased to increase mineral undersaturation.

Many other embodiments are directed to an apparatus for sequestering carbon dioxide, including:
- at least one reactor vessel defining an enclosed volume;
- at least one source of a catalyst, a sequestration agent, a $CO_2$ gas, and an aqueous solution;
- at least one input in fluid communication between the at least one source and the enclosed volume of the at least one reactor vessel; and
- at least one output in fluid communication with the enclosed volume of the at least one reactor vessel;
- wherein the at least one input is arranged such that the $CO_2$ gas and aqueous solution combine to form an aqueous carbon dioxide solution, and wherein the aqueous carbon dioxide solution and catalyst are delivered as a mixture within the enclosed volume of the at least one reactor within a first catalytic region encompassing a second interfacial catalytic region disposed about the sequestration agent and being located within a laminar flow boundary at the interface between the mixture and the carbonate sequestration agent.

In other embodiments at least one of the sequestration agent and catalyst is physically confined within the first catalytic region.

In still other embodiments the sequestration agent is calcium carbonate and the catalyst is a carbonic anhydrase or a carbonic anhydrase analog.

In yet other embodiments the sequestration agent is a non-carbonate sequestration agent.

In still yet other embodiments the aqueous solution is one of either a brine solution or freshwater.

In still yet other embodiments the apparatus further includes at least one enzyme separation filter configured to filter at least catalyst passing therethrough, the separation filter being in fluid communication with at least one output of the at least one reactor vessel.

In still yet other embodiments the apparatus further includes at least one particle filtration system configured to filter at least sequestration agent passing therethrough, the particle filtration system being in fluid communication with at least one output of the at least one reactor vessel. In some such embodiments the particle filtration system comprises a settling chamber in fluid communication with the at least one reactor vessel.

In still yet other embodiments the sequestration agent is formed into grains of 100 micrometers or less.

In still yet other embodiments the apparatus further includes first and second reactor vessels, and wherein an input of the second reactor vessel is in fluid communication with the at least one output of the first reactor vessel, the second reactor vessel being arranged such that an effluent from the first reactor vessel is delivered within the enclosed volume of the second reactor vessel to a second vessel catalytic region wherein a second catalyst is disposed encompassing a second vessel interfacial catalytic region located within a laminar flow boundary at the interface between the effluent and a second carbonate sequestration agent. In some such embodiments the temperature, pressure and pH of the two reactor vessels are independently variable.

In some other such embodiments the second reactor vessel has a lower temperature than the first reactor vessel.

In still yet other embodiments the apparatus further includes a mixing chamber in fluid communication with the inlet of the at least one reaction vessel and wherein the $CO_2$ gas and aqueous solution inputs are mixed prior to introduction into the at least one reaction vessel.

In still yet other embodiments an effluent comprising at least unreacted $CO_2$ from the at least one output is reintroduced into one of the at least one inputs of the reaction vessel.

In still yet other embodiments an effluent from the at least one output has a partial pressure of $CO_2$ lower than the partial pressure of $CO_2$ introduced into the at least one input.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein.

DETAILED DESCRIPTION OF THE INVENTION

Figure 1:
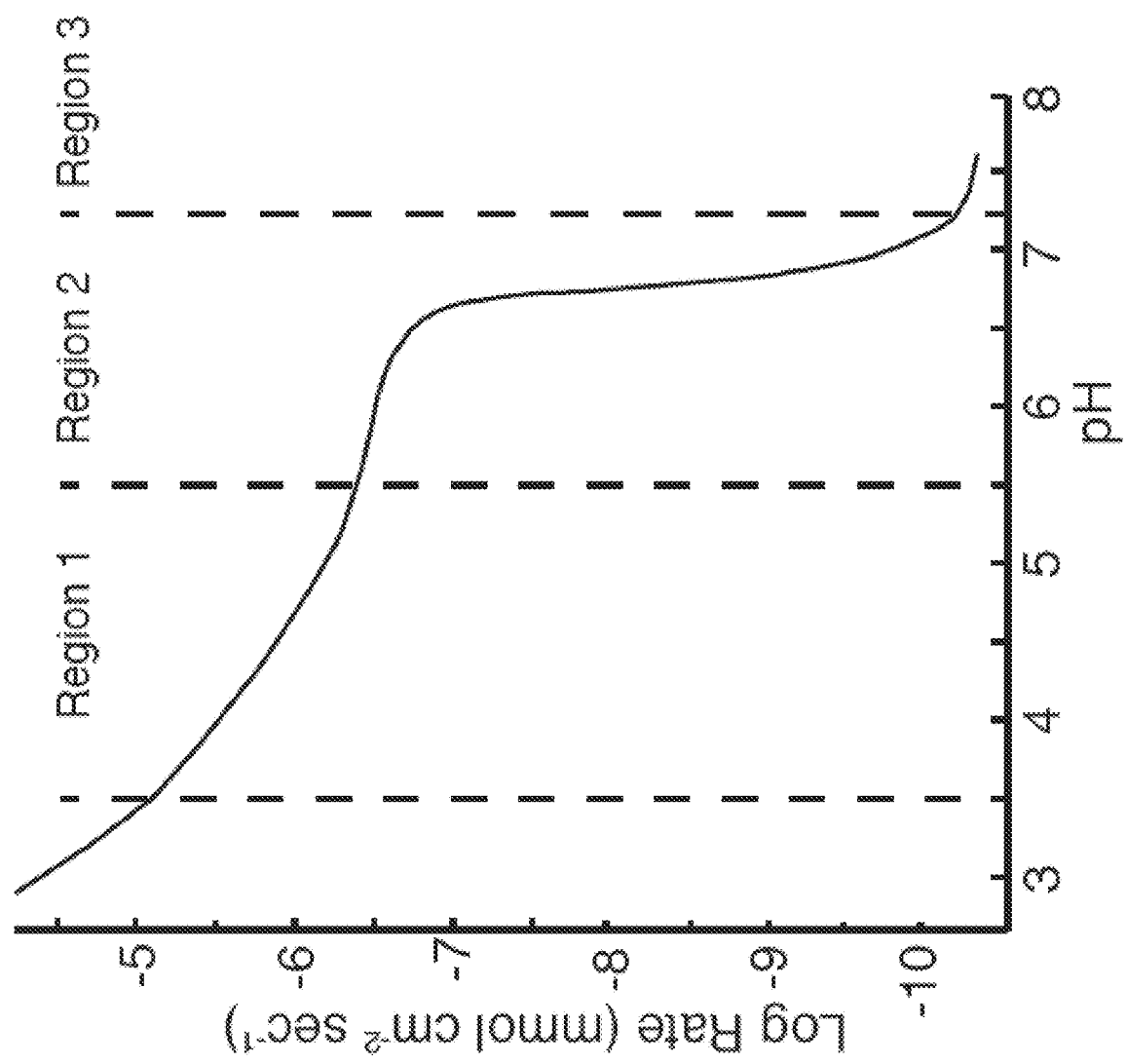
FIG. 1 provides a schematic representation of the rate of dissolution of calcite against pH.

Turning now to the drawings, processes and apparatus for carbon sequestration utilizing a controlled catalyzed sequestration agent reaction in accordance with embodiments of the invention are provided. In many embodiments the system and method for carbon sequestration includes the controlled catalysis of the dissolution of a sequestration agent, such as a mineral sequestration agent (e.g., calcium carbonate), to provide facile and permanent sequestration of $CO_2$ from the gas phase. The process and apparatus comprising the controlled catalysis in accordance with many embodiments allows for the production of an effluent outflow wherein the concentration of $CO_2$ is lower than that found in the reactant inflow. In embodiments, the controlled catalysis processes and apparatus produce a sequestration agent dissolution rate at least greater than the sequestration agent dissolution rate of an uncatalyzed system at the same mineral undersaturation. In various embodiments, the controlled catalysis processes and apparatus produce a sequestration agent dissolution rate at least one order of magnitude greater than the sequestration agent dissolution rate of an uncatalyzed system at the same mineral undersaturation. In other embodiments, the sequestration agent dissolution rate is at least two orders of magnitude greater than the sequestration agent dissolution rate of an uncatalyzed system at the same solution mineral undersaturation. In still other embodiments, the sequestration agent dissolution rate is at least three orders of magnitude greater than the sequestration agent dissolution rate of an uncatalyzed system at the same solution mineral undersaturation. In various embodiments the mineral undersaturation is held at near-equilibrium. In some such embodiments the sequestration agent dissolution involves a carbonate to carbonate ion dissolution. In other such embodiments the dissolution may include one or more sequestration agents including, for example, calcite, aragonite, dolomite and vaterite, silicate mineral etc.

Methods for carbon storage may further involve at least reaction of dissolved $CO_2$ with a sequestration agent (such as, for example, calcium carbonate, aragonite, dolomite, vaterite, etc.) under controlled catalysis conditions to increase the dissolution rate of the sequestration agent at a fixed mineral undersaturation. In embodiments, the concentration of the catalyst in such reactions can be tuned to maximize local protons at the sequestration agent surface to speed the dissolution of the sequestration agent, such as, for example, via one or both of the replenishment of 1) bound protons such as hydrated $CO_2$ (i.e., carbonic acid); or 2) free protons (e.g., from the protolysis of water) from the aqueous $CO_2$ reservoir or $H_2O$ reservoir in proximity to the sequestration agent. In many such embodiments, the methods include the controlled catalytic formation of protons to speed the sequestration agent dissolution, and thus the sequestration reaction of sequestration agent with dissolved $CO_2$.

Many embodiments of methods and apparatus comprise the formation of two-controlled catalysis regions. In many such embodiments, catalytic materials (e.g., enzymes such as carbonic anhydrase) may be introduced in a controlled manner as catalysts to a reactor vessel containing a sequestration agent and a feedstock of aqueous $CO_2$ to create a first catalysis zone or region that encompasses a second interfacial catalysis region proximal to the sequestration agent (e.g., at the interface of the sequestration agent and/or within a laminar boundary layer about the sequestration agent) such that the barrier between the catalysis region and the interfacial catalysis region is minimized.

The kinetics of sequestration reactions in embodiments comprising such two-controlled catalysis regions may be configured in accordance with a number of parameters, which may be independently controlled. In some embodiments of such engineered catalysis methods, the concentration of the catalyst in either or both the catalysis region or the interfacial catalysis region can be configured to optimize the local proton concentration at the interfacial catalysis region, such as, for example, by one or both the replenishment of $H_2CO_3$ (dissolved $CO_2$) from the $CO_2$ aqueous reservoir and/or maximizing the protolysis of water. In other embodiments the temperature and/or pressure within the catalysis region and/or interfacial catalysis region may be increased to increase dissolution rate of the sequestration agent, at a fixed mineral undersaturation, as described above. In some embodiments the concentration gradient of the various reactants (e.g., protons and $CO_2$) can be configured such that a maximum amount of reactant is delivered within the interfacial catalysis region such that in some embodiments the reaction is diffusion limited by the delivery of reactants within the interfacial catalysis region rather than their removal from the interfacial catalysis region.

Turning to the sequestration agent, in some embodiments the sequestration agent may be a mineral material such as for example, carbonates (e.g., metal carbonates), silicates, etc. Suitable calcium carbonates may include any number of such mineral carbonate species, such as, for example, calcite, aragonite, dolomite, vaterite, etc. In various embodiments, one or more such sequestering agents may be used in combination. Accordingly, many embodiments use metal carbonate sequestration agents, while some embodiments use non-carbonate sequestration agents such as for example silicate minerals, and in some further embodiments, sequestration agents include various mineral admixtures. Finally, in yet other embodiments, sequestration agents are a combination of carbonate and non-carbonate solids. Regardless of the specific sequestration agent(s) used, the particle size of sequestration agent may be configured to optimize the surface area of the material, such that, for example, the surface area is increased to increase the exposure of the interfacial catalysis region to the catalysis region, and thereby increase dissolution of the mineral, and minimize the boundary layer between the catalysis region and the interfacial region. Exemplary embodiments utilized milli- or micro-meter scale particles of such sequestration agent materials. Finally, in other embodiments the mineral undersaturation of the sequestration agent can be tuned via manipulation of the temperature, pressure, salinity and/or $CO_2$ (aq) concentration within one or both the catalysis region and interfacial catalysis region, as will be discussed in greater detail below.

In many embodiments, an apparatus may be used to implement a carbon sequestration process as described above. In various embodiments, the apparatus may be comprised of at least a control system to monitor and adjust relevant parameters and at least one reactor whose inputs may include at least $CO_2$ dissolved in an aqueous solution, carbonate, and a catalyst, where the reactor is adapted to form a two-region controlled catalysis zone, wherein a first catalysis region containing a controlled concentration of catalyst encompasses a second interfacial catalysis region in proximity to a sequestration agent (e.g., the laminar boundary layer surrounding the sequestration agent) such that the kinetic rate of hydration and sequestration of carbon are controllable. In many such embodiments, the reactor and the catalysis and interfacial catalysis regions are adapted to catalyze the production of protons (e.g., bound protons or free protons) in the proximity of a sequestration agent (e.g., a calcium carbonate, metal carbonate, silicate, mineral clay, etc.) to increase the rate of dissolution of the sequestration agent and the concomitant production of sequestration agent ions (such as carbonate ions from a metal carbonate such as calcium carbonate. In several embodiments the apparatus is configured to catalyze the dissolution of calcium carbonate in the presence of protons (i.e., free or bound such as carbonic acid) to form calcium and bicarbonate. In many embodiments the catalysis may operate to increase the protolysis of water in the reaction vessel and/or the formation of dissolved $CO_2$ (i.e., carbonic acid).

The reactants, and configuration of such apparatus may be further optimized for each specific sequestration catalysis. Accordingly:

In some embodiments, the aqueous solution may include at least freshwater or seawater and may have a circumneutral pH.

In further embodiments, the catalyst may include any material suitable for the production of protons from the aqueous $CO_2$ solution, including, for example nickel materials and enzymes such as, carbonic anhydrase or a modified carbonic anhydrase, such as may be known in the art.

Within the reactor, there may be a mixing zone where the diffusion boundary layer surrounding the sequestration agent (e.g., carbonate) is decreased (e.g. by stirring, mixing the aqueous solution and/or placing it in a fluidized bed).

Embodiments may contain particles of the sequestration agent in varying sizes. In some exemplary embodiments micrometer scale sequestration agent particles may be used; while in other embodiments larger sequestration agent slabs or beds may be formed.

In some embodiments, metallic carbonates, mineral clays or silicates may be used as a sequestration agent.

Some embodiments may include a feedback loop that controls and continually adjusts mineral undersaturation and the input of catalyst, $CO_2$, and a sequestration agent (such as, for example, $CaCO_3$) such that two controlled and active catalytic regions are preserved within the reaction vessel in the vicinity of the sequestration agent (e.g., at the interface or within a laminar boundary layer about the interface thereof and surrounding such interfacial region) and the sequestration rate efficiency within such catalytic regions are maximized.

In the reactor and the optional feedback loop, at least parameters such as pH, catalyst concentration, and $CO_2$ concentration may also be monitored in embodiments of the invention.

In many embodiments of these systems, one or more of such process parameters may be adjusted such that a rate of carbon sequestration limited only by the diffusion rate of the carbonate ions is achieved, i.e., that the reaction is limited by product transport. In other embodiments the parameters may be controlled to provide an excess of protons: either bound, such as in the form of hydrated $CO_2$ (e.g., carbonic acid) or free, such as from the protolysis of water, such that the sequestration reaction rate is limited by the diffusion of protons and $CO_2$ to the sequestration agent surface, i.e., that the reaction is limited by reactant transport.

Additionally, some embodiments of the invention may also include a second reactor parameterized separately to further neutralize or degas any residual $CO_2$. In embodiments using this second reactor, the input may be the aqueous solution discharged from the first reactor. The second reactor parameters including at least $CO_2$ concentration, aqueous solution input, carbonate saturation, and catalyst input may be monitored and separately controlled in some embodiments. In still other embodiments the apparatus may contain any number or configuration of reaction vessels any one or more of which may be provided with the two-catalysis region configuration in accordance with embodiments.

In further embodiments, filters and other devices are used to retain sequestration agent and/or catalyst within a reactor vessel. For sequestration agent retention, in some embodiments, sequestration agent is retained by filtering effluent water using a particle filtration system. In yet other embodiments, sequestration agent is retained using a settling chamber, which allows reactant to settle so that solid-free effluent water may be discharged. In such embodiments, the settling chamber may be part of a reactor vessel or may be a separately dedicated vessel. In yet further embodiments, a combination of sequestration agent retention strategies may be used. In many embodiments, catalyst is retained using various filtration systems. In some embodiments, catalyst is attached to free-floating solid beads which are retained in the reactor using a particle filtration system or a settling chamber, as described above for the sequestering agent. In some other embodiments, dissolved catalyst is retained using enzyme separation techniques. In still other embodiments, catalyst is replenished using catalyst-expressing organisms, which may be located within or outside the reaction vessel. Such embodiments may also include methods and apparatus for removing/filtering harmful metal or other contaminants that might be contained within the effluent.

In various embodiments, a feedstock enriched in $CO_2$ reacted in accordance with embodiments produces an outflow that has a reduced partial pressure of $CO_2$. In other embodiments the reactor effluent may have slightly enhanced alkalinity, which may be environmentally favorable. In embodiments using seawater, this effluent may be discharged into coastal environments, which may mitigate harmful 'acidified' waters. In embodiments using freshwater and/or brines (e.g. seawater), the effluent may optionally be used for agricultural or commercial uses. In other embodiments the catalyst may be bound to a solid surface, such that the catalyst is not discharged into the environment along with the products from the reaction, or alternatively the catalyst may be filtered out of the effluent. In some embodiments some or all of the active catalyst is allowed to remain in the effluent. In other embodiments catalyst remains in the effluent but is deactivated by heating or other means. In some embodiments the effluent is discharged into the environment. In still other embodiments effluent can be reenriched with $CO_2$ and return to the reaction vessel one or multiple times before it is finally discharged.

Finally, in accordance with still other embodiments of the invention, rates of $CO_2$ hydration for aqueous (or dissolved) $CO_2$ can be altered through one or more methods including but not limited to introduction of a catalyst, altering the flow of the inlet gas stream (i.e., $CO_2$) and increasing the surface area of aqueous solution in contact with a given volume of gaseous $CO_2$.

Review of Carbon Sequestration Approaches

Carbon sequestration involves two steps: carbon capture (impermanent removal of carbon from the atmosphere) and carbon storage (permanent removal from the atmosphere). To mitigate rising levels of $CO_2$, the scale of carbon sequestration must be commensurate with emissions levels. Currently, anthropogenic carbon emissions are roughly 40 gigatons (Gt) of carbon dioxide per year. Because of the magnitude of emissions, for a sequestration strategy to be viable it must be able to keep up with rates of anthropogenic emissions. The carbon sequestration strategies currently available do not permanently sequester carbon at rates sufficient to match amounts of anthropogenic carbon dioxide emissions.

Many carbon sequestration strategies are inadequate because while they provide methods of temporarily capturing $CO_2$, they do not provide methods to permanently store $CO_2$ to prevent it from being released back into the atmosphere. Because carbon sequestration requires both carbon capture and storage, these strategies cannot be said to truly sequester carbon. Examples of carbon sequestration strategies that capture and only temporarily store $CO_2$ are those that primarily involve the dissolution of gaseous $CO_2$ and the hydration of aqueous $CO_2$. Dissolving $CO_2$ gas into water is ineffective for sequestration because once the storage water contacts the atmosphere, the $CO_2$ in solution will begin to degas out of solution. Moreover, this process is relatively rapid, occurring in some cases over a period of months to weeks to hours. As a result, and as will be discussed in greater detail below this rapid degassing requires secondary storage requirements, such as, for example, ground water injection to prevent release of carbon back into the environment.

The reason for the temporary nature of many conventional methods of capturing $CO_2$ relates to the nature of how they are attempting to "store" $CO_2$. In particular, the general strategy in these methods is to increase the "hydration" of $CO_2$ (i.e., the dissolution of $CO_2$ into solution thereby increasing the amount of $CO_2$ that, in theory, is being taken out of the atmosphere. In true hydration, carbon is captured as carbonic acid ($H_2CO_3$), in accordance with the reaction below,

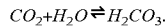

However, the reaction dynamics of dissolving $CO_2$ into solution are complicated and the true hydration of $CO_2$ to carbonic acid ($H_2CO_3$) is a relatively minor component of the overall reaction. Specifically, the hydration of $CO_2$ (i.e., the formation of carbonic acid) is very slow, and this hydration is also much slower than the dehydration of $CO_2$, i.e., the reversion of carbonic acid to $CO_{2(aq)}$. This is because the reaction thermodynamics are highly unfavorable to the formation of $H_2CO_3$. Accordingly, a solution of hydrated $CO_2$ usually contains mostly $CO_{2(aq)}$, with very small amounts of $H_2CO_3$. For example, the value for $K_{eq}$ for $H_2CO_3$ and $CO_{2(aq)}$ is 0.0015 at 25° C. and 1 atmosphere pressure. Accordingly, the ratio of $CO_{2(aq)}$:$H_2CO_3$ at room temperature is around 670. For this reason, sequestration strategies that focus on "hydration" largely result in solutions of $CO_{2(aq)}$. Accordingly, the term $H_2CO_3^*$ is often used to describe the aqueous mixture of $CO_2$ and $H_2CO_3$ formed by such hydration reactions, where $H_2CO_3^*$ is the sum of the other two species. In short, many sequestration strategies that focus on hydration involve the formation of $H_2CO_3^*$, not $H_2CO_3$.

Furthermore, because the thermodynamics are so unfavorable, if a solution contains large amounts of $CO_{2(aq)}$ for the purpose of driving hydration, degassing is likely to occur. As a result, there is high likelihood that $CO_{2(aq)}$ will leave solution and return to gaseous $CO_2$ when it contacts the atmosphere. Moreover, as $[CO_{2(aq)}]$ decreases due to degassing, kinetics also becomes a factor making hydration even less favorable. Thus the dissolution of $CO_2$ into solution, or the "hydration" of $CO_2$ by itself does not constitute sequestration because it is a dynamic process where $CO_2$ is constantly dissolved into and released back into the environment, and so does not effectively store the reacted $CO_2$ in a permanent manner, unless the fluid is permanently isolated from the environment, such as by being injected into an impermeable storage reservoir. The drawback of such systems is that they are subject to leaks and so require constant monitoring and mitigation measure to detect and prevent leakage back into the environment.

To more effectively store $CO_2$ permanently it can be reacted with something to chemically fix the $CO_2$. Examples of sequestering $CO_2$ in this manner include organic carbon fixation (i.e., photosynthesis) and reaction with a sequestration agent such as limestone. Carbon fixation from photosynthesis is the fixation of gaseous $CO_2$ in a series of reactions known as the Calvin cycle. However, even this photosynthetic reaction does not provide a permanent way to fix carbon because the trees or plants into which the $CO_2$ is being stored will eventually die and when they do, the carbon stored in the plant matter will return to the atmosphere through respiration by termites and microbes. In contrast, through reaction with limestone ($CaCO_3$), the planet will naturally consume nearly all of the anthropogenic $CO_2$ emissions in the following reaction:

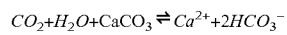

In nature, this reaction takes place in the deep ocean where undersaturated waters are in contact with carbonate bearing sediments. However, the kinetics of this reaction are very slow. There are kinetic limitations in the ocean-atmosphere-sediment system, some of which are related to reactant transport (Archer et al., *Global Biogeochem. Cy* 12:259-276 (1998), the disclosure of which is incorporated herein by reference). Initially, the exchange of $CO_{2(g)}$ with $CO_{2(aq)}$ at the ocean surface will take a few hundred years. Next, the $CO_{2(aq)}$ at the surface must travel from the surface to the deep ocean, a process that takes an order of 1000 years. And finally, when the $CO_{2(aq)}$ reaches ocean sediments, it must react with $CaCO_3$ which occurs on a timescale of several thousand years. In total, it is estimated that the e-folding timescale for these processes is 6800 years (Archer et al., 1998, cited above). As can be seen, both of these natural reaction processes have serious drawbacks related to reactant transport and will not be effective on the types of anthropogenic time-scales necessary to address anthropogenic $CO_2$ emissions.

Apart from the kinetic challenges associated with reactant transport in the natural environment, dissolution itself is very slow. The following equation illustrates the hydration of $CO_2$ and how concentrations of carbonic acid and carbonate ions are closely linked by simple acid-base reactions:

$$CO_2+H_2O \rightleftharpoons H_2CO_3 \rightleftharpoons {}^++HCO_3{}^- \rightleftharpoons 2H^++CO_3{}^{2-}$$

The kinetics of calcium carbonate dissolution are typically described by the equation:

$$\text{Rate}=k(1-\Omega)^n$$

where $\Omega$ is a mineral's saturation state, which is defined as the product of effective in situ calcium and carbonate ion concentrations divided by the apparent solubility product for that mineral ($[Ca^{2+}][CO_3{}^{2-}]/K'_{sp}$); k is a rate constant; and n is the reaction order. The reaction order has no physical or chemical significance; it solely describes an empirical relationship between saturation state and the dissolution rate. In this set of equations thermodynamic potential, or mineral undersaturation, $(1-\Omega)$ drives the dissolution rate.

Attempts have been made to augment the kinetics of carbonate dissolution, but thus far have not succeeded in designing effective or practicable solutions. For example, attempts were made to increase the geological rate of dissolution observed in the water column by reacting $CO_2$ with limestone at the surface of the earth thereby removing the delay caused by the transport of reactants from the surface of the ocean to the bottom of the ocean. In a process described in U.S. Pat. No. 7,655,193, a reactor charged with limestone pellets and designed to keep a steady stream of $CO_2$ dissolved in seawater might reasonably be able to maintain 30% mineral undersaturation (equivalent to equilibrating seawater with gas containing about $pCO_2$ of about 4,000 ppm) to achieve a dissolution rate of $6 \cdot 10$ g/cm$^2$/day (Subhas et al. Geochimica et Cosmochimica Acta, Volume 170, 1. (2015), pgs 51-68, the disclosure of which is incorporated herein by reference). However, even using very high $[CO_2]$ gas (10% v/v) and a 1-2 week reaction time, the process disclosed in U.S. Pat. No. 7,655,193 only manages to achieve a dissolution rate of $6 \cdot 10^{-5}$ g/cm$^2$/day. (See, e.g., Rau, G. H. (2011). Environmental Science & Technology, 45(3), 1088-1092, the disclosure of which is incorporated herein by reference.)

Operating on a global scale, the aforementioned rates of carbonate dissolution are simply too slow to adequately address the current levels of $CO_2$ emissions. Applied to the sequestration of 40 Gt of $CO_2$ emitted annually, such a system would require a large amount of calcium carbonate to be dissolved in tens to hundreds of thousands of reactor factories around the world. For example, dissolving enough limestone to annually titrate 40 Gt of $CO_2$ using a conventional system would require a cube of limestone that is roughly 2 miles on each side. Daily, this would require $2.5 \cdot 10^{14}$ g of $CaCO_3$ to be dissolved. Using reactors similar to those described in U.S. Pat. No. 7,655,193 having a 2 m$^3$ volume, containing 1 m$^3$ of $CaCO_3$ broken up into 1 mm$^3$ cubes, and at 30% mineral undersaturation, the dissolution reaction would require 70 billion reactors. To further illustrate the scale of implementing a sequestration method operating at this rate, if the 2 m$^3$ reactors were placed in factories sized 300 m×600 m×10 m, this would still require 767,000 factories. Operating at the maximum rate describe in the U.S. Pat. No. 7,655,193 patent, the number of factories would only decrease by a factor of 10. As can be seen from the above illustration, the sheer magnitude of the amount of $CO_2$ to be dissolved requires a faster rate of dissolution for this method of sequestration to be practical.

Mineral undersaturation can be achieved by increasing $[CO_{2(aq)}]$, decreasing solution temperature, increasing solution pressure, and/or pumping pressurized $CO_2$ gas into the aqueous solution to allow for greater dissolution of $CO_2$. However, there are other impracticalities related to relying on high concentrations of $CO_{2(aq)}$ alone to increase reaction rates. In particular, the type of cool, pressurized, high $[CO_{2(g)}]$ gas streams required need significant inputs of energy to create. To save energy, sequestration could be integrated into preexisting industrial processes. In an industrial setting, however, one is unlikely to encounter cool, pressurized, high $[CO_{2(g)}]$ gas effluent streams, because most effluent streams that are rich in $CO_2$ are unlikely to be cool. On the other hand, with high temperature streams, it is difficult to keep the $CO_2$ in solution without expending large amounts of energy, which may negate any of the benefits of the sequestration strategy related to carbon emissions. Therefore, relying on gaseous undersaturation alone to drive sequestration would lead to a very inefficient and impractical process.

Embodiments of the present invention are directed to systems, methods and processes that use a carefully engineered catalysis reaction at the interfacial reaction zone between hydrated $CO_2$ and a sequestration agent to increase the rate of sequestration agent dissolution for faster sequestration, providing a feasible approach to sequestration agent dissolution. In some embodiments of the proposed invention, the sequestration rate may be made independent of the saturation state of the mineral such that far from equilibrium mineral undersaturation is not necessary to increase reaction rates substantially above those presently described in the art. As a result, embodiments of the invention can be more practically implemented than others requiring high mineral undersaturation.

Description of Catalyzed Sequestration Parameters

The mechanism and rate of sequestration is typically defined by the rate of carbonate production. As schematized in FIG. 1, the rate of carbonate dissolution in seawater depends directly on the alkalinity/pH/DIC of the solution (e.g., mineral undersaturation). At low alkalinity (low pH, e.g., Region 1 and below), the rate of carbonate production is limited to proton attack only. By contrast, as the Alkalinity:DIC ratio increases (where mineral undersaturation is not so high and $CO_2$ is in equilibrium with alkaline water, e.g., Region 2) the uncatalyzed dissolution rate begins to decline independent of transport control. At "circum-neutral" pH ranges (e.g., between regions 2 and 3) there is an extreme drop-off, which generally prevents the efficient sequestration of $CO_2$ within these high pH (e.g., near-equilibrium undersaturation) regimes. In embodiments of this invention it has been found that protons, and more specifically the presence of either free (e.g., from protolysis of water) or bound (e.g., carbonic acid) protons introduced into a catalysis reaction region in proximity to a sequestration agent, increases the dissolution rate of the sequestration agent and plays an important mechanistic role in the permanent sequestration of $CO_2$, particularly in environments like seawater, such that sequestration rates can be increased such that they are, in some embodiments, transport limited even in equilibrium undersaturation regimes (e.g., circum-neutral pH ranges). In other words, it has now been discovered that dissolution rates in Region 3 can be enhanced by utilizing the controlled catalysis methods and apparatus in accordance with embodiments to behave more like dissolution rates in Regions 1 and 2.

Conventional mechanistic models have focused on specific carbonate species and their interaction with the mineral surface. In general, these mechanistic equations are made up of multiple terms, each with first-order dependence. (See, e.g., Plummer, L. N., Wigley, T., 1976. Geochimica et Cosmochimica Acta 40 (2), 191-202; Shiraki, R., Rock, P. A., Casey, W. H., 2000. Aquatic Geochemistry 6, 87-108;

Gledhill, Dwight K., and John W. Morse. *Geochimica et cosmochimica acta* 70.23 (2006): 5802-5813; Finneran, David W., and John W. Morse. *Chemical geology* 268.1 (2009): 137-146; Arakaki, Takeshi, and Alfonso Mucci. *Aquatic geochemistry* 1.1 (1995): 105-130, the disclosures of which are incorporated herein by reference.) The dissolution of calcite in dilute solution can be described using three main regimes: one transport-controlled regime dominated by hydrogen ion attack and diffusion, and two surface-controlled regimes controlled by proton (either $H_2CO_3$ (carbonic acid) or water) attack. As described above with respect to FIG. 1, different sequestration systems may harness different reaction mechanisms. In solutions of high pH and low $pCO_2$ (like seawater, for example), the Plummer and Wigley's 1976 study proposed that water attack is the main dissolution mechanism. It was also thought that $H_2CO_3$ attack was valid at high $pCO_2$. Later, it was thought that a multicomponent dissolution mechanism in which hydrogen ion, bicarbonate ion, and hydroxide ion all function as dissolving agents in different pH regimes was the best model (Shiraki, 2000). In seawater conditions the dominant dissolution mechanism was thought to be bicarbonate attack, where a bicarbonate ion acts as a nucleophile, and performs a nucleophilic attack on a hydrated calcium ion on the mineral surface. Despite the fact that $H_2CO_3$ is the most acidic of the carbonate species, it was not implicated as part of the standard seawater dissolution mechanism. Another mechanistic model proposed that in the region of seawater pH, $H_2O$ and $H_2CO_3$ activities determine the dissolution rate of calcite (Plummer and Wigley, 1976). Here again, the role of $CO_2$ hydration kinetics in dissolution rate was not considered.

In particular, in these conventional methods, the kinetics of $CO_2$ hydration and its relationship to solid phase dissolution rate were not considered. By contrast, in embodiments of sequestration systems, methods and apparatus, proton species (free or bound such as $H_2CO_3$) have now been identified as the dominant species involved in the dissolution of sequestration agent, and methods and apparatus are provided to persistently increase its standing stock in proximity thereto. In short, true rates of proton production (e.g., hydration of $CO_2$ to carbonic acid or protolysis of water) are catalytically enhanced, and then the proton concentration is preserved and controllably presented directly at the source of sequestration agent to maximize the dissolution rate at a fixed mineral undersaturation, and particularly at mineral undersaturations previous thought to be so close to equilibrium so as to be too slow. Thus, in embodiments where the sequestration agent is a carbonate, such as, for example, $CaCO_3$, mechanistically the dissolution of the carbonate sequestration agent can be expressed as:

$$CaCO_{3(s)} + H_2CO_3 \rightarrow Ca^{2+} + 2HCO_3^-$$

Depending on in situ pH and other factors, the reaction products may include carbonate ion ($HCO_3^-$) or alternatively metal carbonate (such as, for example, calcium bicarbonate ($Ca(HCO_3)_2$)). For the purposes of this application, carbonate ion and bicarbonate may be used interchangeably.

The chemical underpinning of this reaction is fundamentally different than previous attempts at carbon dioxide sequestration both conceptually and in application, Using engineered catalysis schemes, embodiments of the system, process and apparatus increase the rate of conversion of CO2(aq) and water to active dissolution agents (i.e., protons) at the source of sequestration agent without necessarily requiring a concomitant increase in the mineral undersaturation allowing for a dramatic increase in the overall rate of $CO_2$ sequestration achievable.

Though the presence of protons (free or bound) has now surprisingly been discovered to be the dominant species involved in carbonate dissolution, they are often in short supply because, as described above, hydration is a very slow kinetic step. The hydration reaction can be expressed in the following equation:

$$CO_{2(aq)} + H_2O \leftrightarrow H_2CO_3$$

Uncatalyzed, in an aqueous solution, the rate of dehydration has been shown to exceed the rate of hydration by a factor of ~1000 under some conditions (Wang, Xiaoguang, et al. *The Journal of Physical Chemistry A* 114.4 (2009): 1734-1740, the disclosure of which is incorporated herein by reference). Thermodynamically, then, there is a very strong tendency for $H_2CO_3$ to dissociate to $CO_{2(aq)}$ and, if exposed to the atmosphere, for $CO_{2(aq)}$ to degas to $CO_{2(g)}$. Carbonic acid can also undergo acid-base reactions to form bicarbonate ($HCO_3^-$) and carbonate ($CO_3^{2-}$) ions. So, for a fixed concentration of $H_2CO_3^*$, the equilibrium abundance of $CO_{2(aq)}$ outweighs the abundance of $H_2CO_3$ by a very large factor.

Accordingly, systems that focus on increasing $H_2CO_3^*$ for sequestration will be unable to sequester carbon at higher rates, and because of thermodynamics, the standing stock of $H_2CO_3$ will likely to be very low. The standing stock will be even lower if dissolution of a sequestration agent (such as carbonate) consumes $H_2CO_3$ much faster than it is produced. A relatively low standing stock of $H_2CO_3$ will, in this example, prevent higher rates of carbonate dissolution and thus lower the kinetic rate of sequestration.

Certain enzymes have been shown to catalyze the hydration of $CO_2$. These enzymes include, but are not limited to, carbonic anhydrase. The actual mechanism of carbonic anhydrase was shown by Silverman and Lindskog (1988) to essentially catalyze the protolysis of water:

$$H_2O + CO_{2(aq)} \leftrightarrow OH^- + CO_{2(aq)} + \text{enzyme-}H^+ \leftrightarrow HCO_3^- + \text{enzyme-}H^+ \leftrightarrow H_2CO_3 + \text{enzyme},$$

where the "enzyme" is carbonic anhydrase, but could be, any molecule or material that performs this set of chemical transformations. The enzyme transports the proton away from the active site to the solution, where it can later react with the newly formed bicarbonate ion. Thus the enzyme does at least four critical things: (1) it protolyzes water into hydroxide ion and protons; (2) it transports the proton away from the active site to the bulk solution; (3) it reacts carbon dioxide with hydroxide ion to form bicarbonate; and (4) it releases bicarbonate to later recombine to form carbonic acid. This gives the reaction mechanism with carbonate two options. In one, carbonate (such as for example calcium carbonate) dissolves through interaction with an enzyme (such as for example carbonic anhydrase), for example:

$$CaCO_{3(s)} + H_2CO_3 \rightarrow Ca^{2+} + 2HCO_3^-$$

In another, carbonate dissolves through interaction with protons at circum-neutral pH, for example:

$$CaCO_{3(s)} + H^+ + HCO_3^- \rightarrow Ca^{2+} + 2HCO_3^-$$

In view of the above, embodiments of the proposed invention rely on a novel kinetic and mechanistic formulation of carbonate dissolution to provide an engineered system with enhanced rates of carbonate dissolution. Embodiments, methods and apparatus, are provided incorporating catalysis schemes configured to provide high concentrations of protons, (e.g., free protons or bound protons, such as hydrated $CO_2$) in proximity with a sequestration agent, such as, for example, a carbonate, such that the kinetics of hydration and carbonate dissolution are enhanced, while the mineral undersaturation (1−Ω) remains fixed (i.e., does not require high levels of undersaturation or undersaturation far from equilibrium). In some embodiments, concentrations of carbonic acid and or free protons are fine-tuned in an interfacial catalysis region proximate to the sequestration agent (e.g., carbonate surface) interface (e.g., within the laminar boundary layer of the sequestration agent surface). This is to be contrasted with conventional $CO_2$ hydration systems, which rely on the assumption that dissolution is driven solely by gaseous saturation state of aqueous $CO_2$, i.e., by trying to increase mineral undersaturation. Accordingly, embodiments of the methods and apparatus of the current system using two-region the controlled catalytic methods are capable of driving the reaction rate of $CO_2$ sequestration even in the absence of strong mineral undersaturation.

Catalyzed Sequestration Process Embodiments

Many embodiments of the invention are directed to sequestration processes that provide increased rates of carbon sequestration by creating at least two controlled catalyzed regions in proximity to a sequestration agent (such as $CaCO_3$). A schematic of a process in accordance with embodiments utilizing a $CaCO_3$ sequestration agent is provided in FIG. 2 and will be discussed in greater detail below. In these embodiments, for example, the slow reaction steps of hydration and dissolution are enhanced to provide an excess of hydrated $CO_2$ in the form of carbonic acid at an interfacial region of the sequestration agent to maximize mineral dissolution rates at a fixed mineral undersaturation. In embodiments, of this system, a reaction driven by the presence of a suitable catalyst, such as, for example, carbonic anhydrase, controllably introduced into a reaction vessel, is utilized to enhance the rate of proton production (e.g., water protolysis and $CO_2$ hydration) and increase the bulk concentration of protons in solution in a specific catalyzed region such that the concentration of protons present within an second interfacial catalysis region (defined in some embodiments as a region surrounding the solid sequestration agent and in other as the laminar boundary layer of the sequestration agent) is sufficient to maximize the dissolution of the sequestration agent independent of the mineral undersaturation (e.g., at equilibrium mineral undersaturations).

Figure 3:
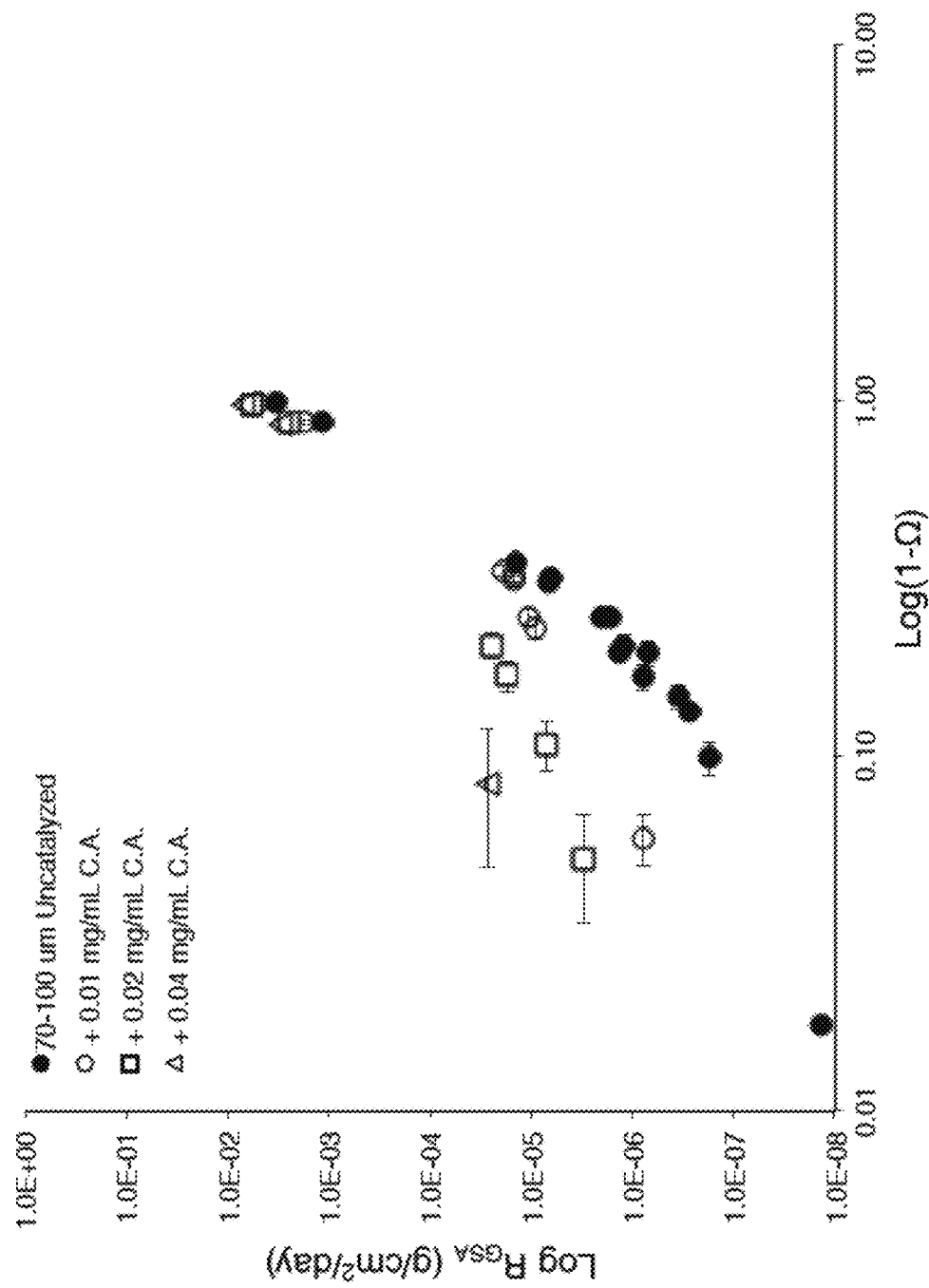
FIG. 3 provides a data graph plotting the rate of sequestration versus calcite undersaturation in accordance with conventional sequestration methodologies and embodiments in accordance with the invention.

To understand the operating principal behind embodiments of these methods and apparatus it is necessary to understand the difference between the conventional uncatalyzed approaches to $CO_2$ sequestration and those disclosed in accordance with embodiments. FIG. 3, provides a graphical demonstration of these differences. As shown, in seawater, the rate of carbonate dissolution can be enhanced by several orders of magnitude by conducting dissolution in the presence of a suitable catalyst (such as, for example carbonic anhydrase), that is by creating a controlled catalyzed region in proximity to the interface between the carbonate sequestration agent and the $CO_2$ solution. Other systems use catalysts like carbonic anhydrase to simply increase the concentration of dissolved carbon dioxide, but in these systems there is potential for degassing because sequestration does not occur immediately after hydration. Embodiments of the claimed process use catalysis in a fundamentally different manner. Instead of using catalysis to increase $[H_2CO_3^*]$, catalysis is used to produce protons (both free and in the form of hydrated $CO_2$) within an interfacial catalysis region surrounding the sequestration agent thereby increasing the rate of mineral dissolution of the sequestration agent without the need for an increase in mineral undersaturation (e.g., a mineral undersaturation far from equilibrium).

Examining the data in FIG. 3 in more detail it is shown that uncatalyzed dissolution can be extrapolated to complete mineral undersaturation to get a maximum possible rate of $2.5×10^{-3}$ $g/cm^2/day$. The carbonate ion transport limitation is ~$3×10^{-3}$ $g/cm^2/day$ (assuming a boundary layer thickness of 10 microns). Accordingly, this data demonstrates that using conventional sequestration schemes without the carbonate catalysis systems and methods in accordance with embodiments there must be complete mineral undersaturation (which as will be discussed in greater detail below is an impossibility) to sequester $CO_2$ efficiently.

In contrast, FIG. 3 shows that dissolution rates for carbonate catalyzed systems and methods in accordance with embodiments approach $1×10^{-4}$ $g/cm^2/day$ to $1×10^{-3}$ $g/cm^2/day$ at mineral undersaturation (1−Ω) values of far from complete mineral undersaturation (e.g., from 0.5 to as low as 0.1). Accordingly, using embodiments of the catalyzed systems and methods described, catalysis rates can approach the physical maximum possible in natural waters. As such, this data demonstrates that using the catalysis systems and methods and minimizing reactant transport, by operating such catalysis within a defined catalysis region such that catalyzed reactant can interact within an interfacial catalysis region in proximity with the sequestration agent, the systems and methods sequester carbon much faster than previously observed. Indeed, the reaction rate approaches the diffusion limit in a way that other sequestration methods, particularly those that emphasize $CO_2$ dissolution and hydration, are simply not capable of attaining. Not to be bound by theory, but in some embodiments it is possible through the use of catalysis in the system described to achieve sequestration rates that reach the diffusion limit (e.g., in some embodiments exceed a dissolution rate of $2.5$ $10^{-3}$ $g/cm^2/day$). In many embodiments, the catalysis can be run at an equilibrium mineral undersaturation (e.g., at a pH of 4.5 or higher and in some embodiments as high as 6 or higher) and achieve dissolution rates of from $1·10^{-4}$ $g/cm^2/day$ to $1·10^3$ $g/cm^2/day$.

Figure 4A:
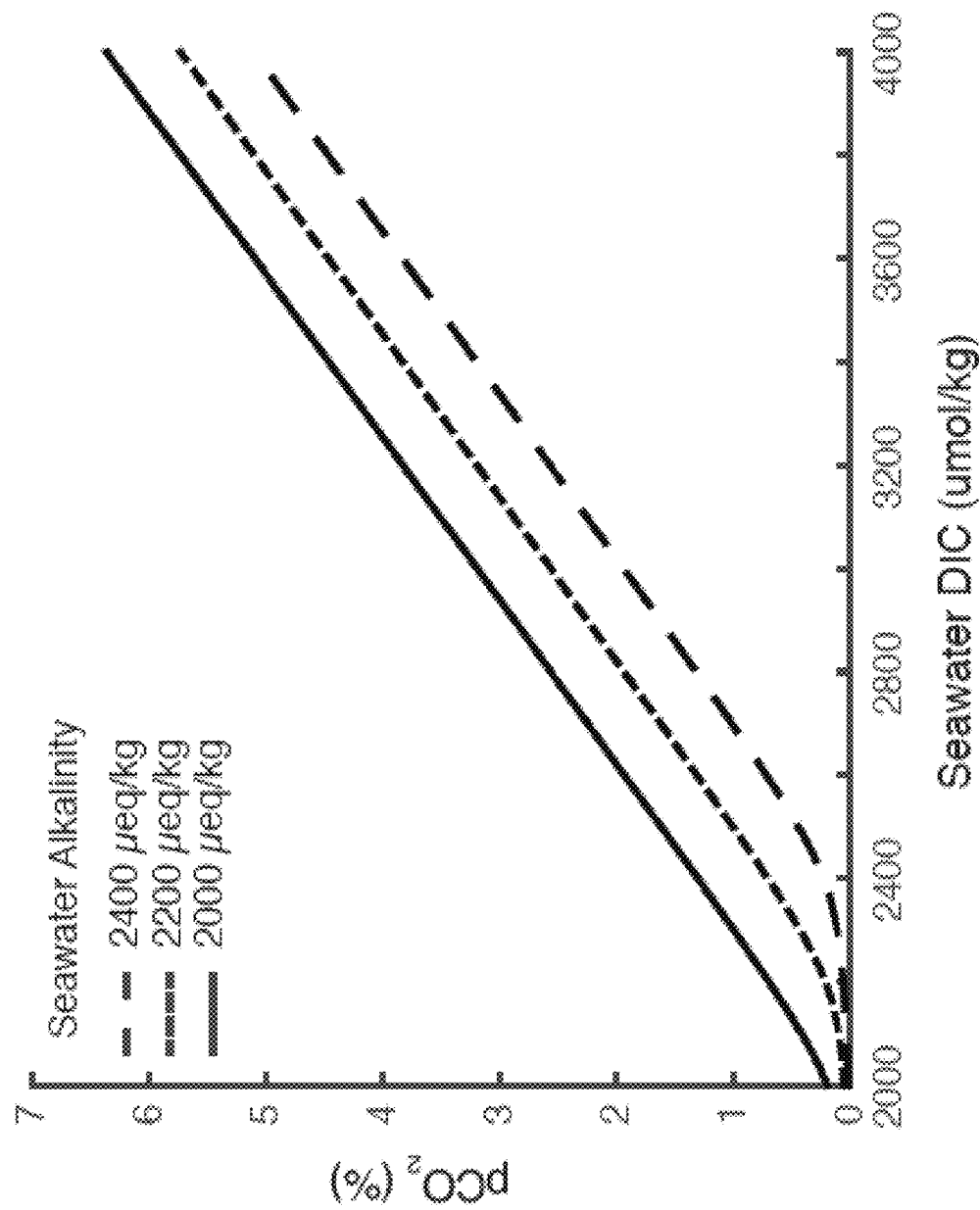
FIG. 4A provides a data graph plotting $pCO_2$ versus dissolved inorganic carbon (DIC) for different values of Alkalinity (Alk)
Figure 4B:
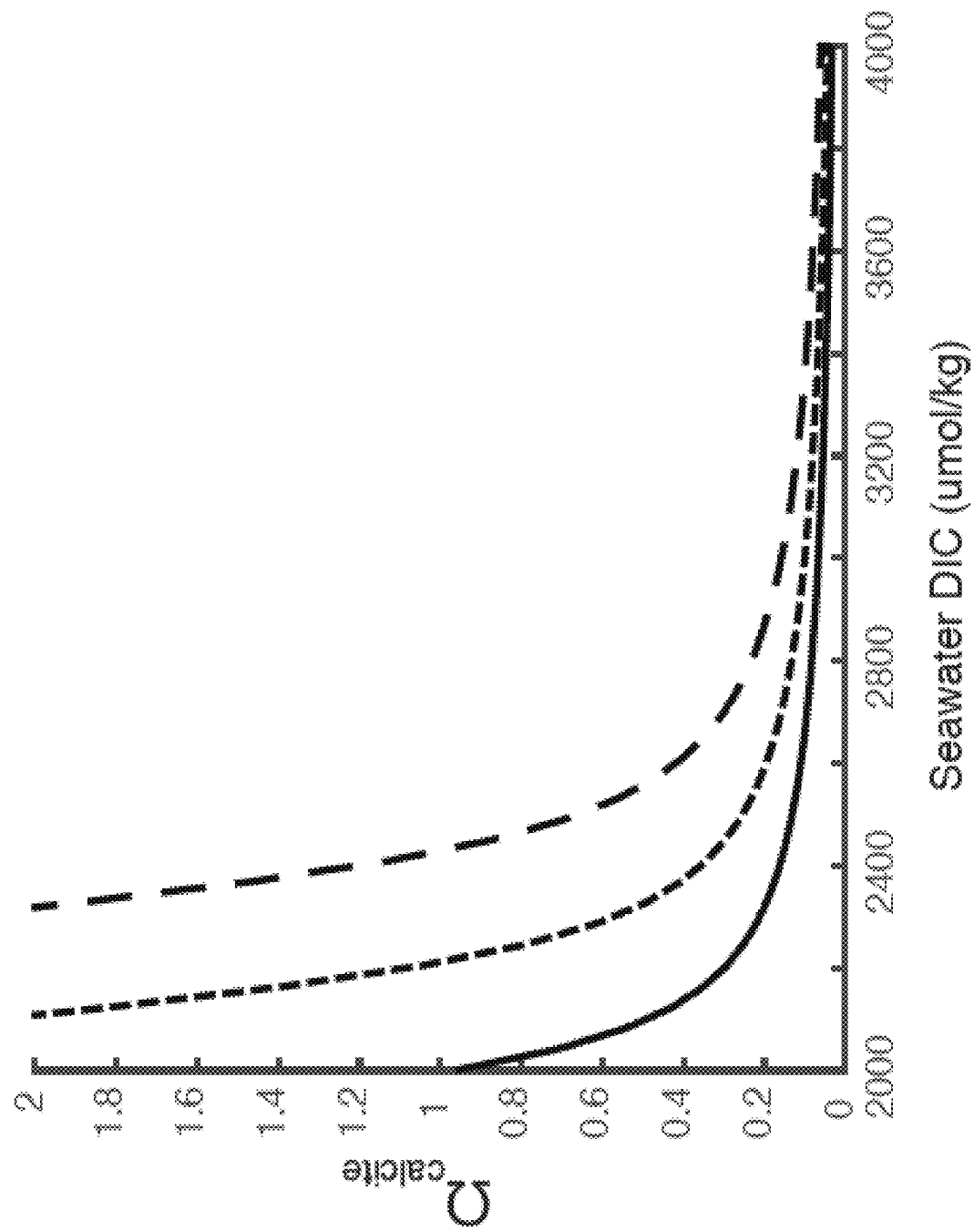
FIG. 4B provides a data graph plotting mineral undersaturation versus dissolved inorganic carbon (DIC).

As described above, in conventional sequestration systems it is necessary to approach complete mineral undersaturation (i.e., a 1−Ω value of 1) to achieve the rates of sequestration obtained using embodiments of the current catalyzed system. FIGS. 4A and 4B provide calculations that illustrate the difficulty in achieving complete mineral undersaturation in seawater. At standard seawater ranges of mineral undersaturation, dissolution kinetics are slow (1e-6 to 1e-5 $g/cm^2/day$). To achieve much higher rates of dissolution, 1−Ω must approach 1. The calculated data in FIGS. 4A and 4B show that this is not physically possible. As observed in a theoretical calculation with $CO_2$ injection at fixed alkalinity like those found in seawater (FIG. 4A), as DIC is increased the saturation state plateaus to a lower, but non-zero, value of Ω (FIG. 4B). Even at very large DIC enrichments (high $pCO_2$) (FIG. 4A), complete mineral undersaturation is impossible through dissolving gaseous $CO_2$ into seawater alone. Accordingly, conventional systems that attempt to increase sequestration rates by increasing $CO_2$ concentration in solution (i.e., gaseous undersaturation) simply are not capable of reaching the rates of sequestration provided in the systems, methods and apparatus described in embodiments of the invention.

Figure 5:
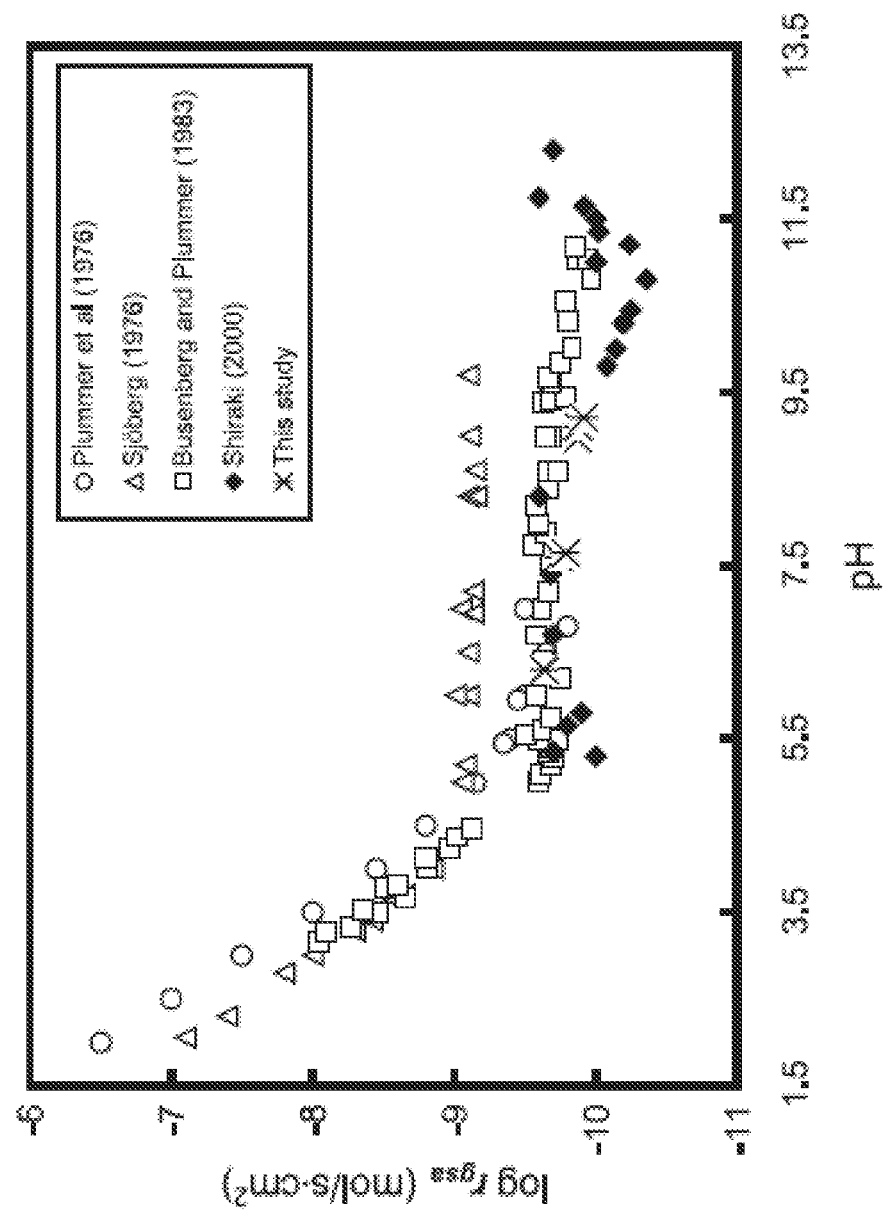
FIG. 5 provides a data graph adapted from Cubillas (Cubillas et al., *Chem. Geo.*, 216:59 (2005)) plotting dissolution rate of calcite versus pH.

As described above with reference to FIG. 1, typically, the diffusion limit is calculated for the transport of reaction products away from the surface. In embodiments according to the systems, methods and apparatus, the diffusion limit may be calculated for transport of the sequestration agent (e.g., metal bicarbonate, i.e., calcium bicarbonate) away from the surface sequestration agent. If instead the reaction may be limited by the transport of the reactants to the sequestration agent surface as in some embodiments of systems and methods in accordance with the invention, it would be possible to speed up the sequestration of carbon even further. Although such a reactant transport limitation has been described in other studies, these studies typically require an extremely low pH for carbonate dissolution, through reaction with hydronium ion (as shown and described in FIG. 5, taken from Cubillas, P., Kohler, S., Prieto, M., Chairat, C., Oelkers, E. H., 2005. *Chemical Geology* 216 (1-2), 59-77, the disclosure of which is incorporated herein by reference. As further shown in FIG. 5, at low pH (below 5), the dissolution rate of carbonate is linearly related to $H^+$ concentration and is commonly interpreted as the transport limitation of $H^+$ to the mineral surface. FIG. 5 illustrates the difficulty in driving high dissolution rates at pH values greater than 5. Thus, this shows that, optimally, to increase dissolution (and hence sequestration) rates, the pH should be lowered as much as possible, preferably below 5.

In reality it is nearly impossible to drive seawater pH to values less than 5 with the addition of gaseous $CO_2$ alone. So, in other systems which emphasize maximizing $[H_2CO_3^*]$ in solution prior to reaction with carbonate, rates of dissolution would be slow, consistent with dissolution rates for circum-neutral solution. Also, in media like seawater it is difficult to drive mineral saturation values ($\Omega$) to less than 0.2. Indeed, as shown and described in FIG. 4B, even with the addition of acid (lower alkalinity), it is impossible to reach complete mineral undersaturation. Accordingly, in conventional sequestration systems there must be complete mineral undersaturation to sequester $CO_2$ efficiently. However, as discussed, using a controlled catalyzed system as described in embodiments of the systems, methods and apparatus it is possible to achieve high rates of carbon sequestration without requiring high levels of mineral undersaturation or extremely low pHs by instead engineering a method and/or apparatus in which the sequestration reaction occurs within a catalyzed region whereby protons (e.g., free protons or bound protons in the form of carbonic acid) are present at an interfacial catalysis region surrounding the sequestration agent (e.g., surface of mineral carbonate) to thus increase mineral dissolution, reduce the need for substantial reactant transport, and reduce the possibility of dehydration of the carbonic acid and degassing of the $CO_2$ from solution even at mineral undersaturation regimes near equilibrium.

Accordingly, although specific embodiments of methods and apparatus in accordance with embodiments are described, regardless of the specific design of the reaction vessel and catalysis regions disposed within the reaction vessel, the controlled catalysis methods and apparatus form two catalysis regions: a first catalysis region where catalyst and $CO_2$ (aq) can combine in a controlled manner and a second interfacial catalysis region defined by the interface between the surface of the sequestration agent and the surrounding solution (e.g., the laminar boundary layer of at the sequestration agent surface). In such a two catalysis region set-up the concentration of catalyst, $CO_2$ (aq), temperature and pressure, flow rate, $CO_2$ (gaseous) injection rate, etc. can be tuned to: 1) maximize the dissolution rate of the mineral, and 2) maximize the replenishment of protons (e.g., free protons from the protolysis of water and/or $H_2CO_3$ from the $CO_2$(aq) reservoir) from the first to the second interfacial catalysis region. Using such a two-region catalysis zone reaction method and vessel, the concentration of protons in the solution delivered to the sequestration agent can be maximized and replenished at the sequestration agent (e.g., carbonate, mineral clay, silicate, etc.) surface. In many embodiments, such processes and apparatus produce a dissolution rate of sequestration agent within the interfacial catalysis region greater than the dissolution rate of sequestration agent in an uncatalyzed system at the same mineral undersaturation. In many embodiments, such processes and apparatus produce a dissolution rate of sequestration agent within the interfacial catalysis region at least one order of magnitude greater than the dissolution rate of sequestration agent in an uncatalyzed system at the same mineral undersaturation. In other embodiments, the sequestration agent dissolution rate within the interfacial catalysis region is at least two orders of magnitude greater than the sequestration agent dissolution rate of an uncatalyzed system at the same mineral undersaturation. In still other embodiments, the sequestration agent dissolution rate within the interfacial catalysis region is at least three orders of magnitude greater than the sequestration agent dissolution rate of an uncatalyzed system at the same mineral undersaturation. In any of the above embodiments the mineral undersaturation of the system may be held near equilibrium. In still other embodiments the system may be run in a circum-neutral conditions (e.g., at a pH greater than 4.5 and in some embodiments from pH 4.5 to pH 7).

Figure 2:
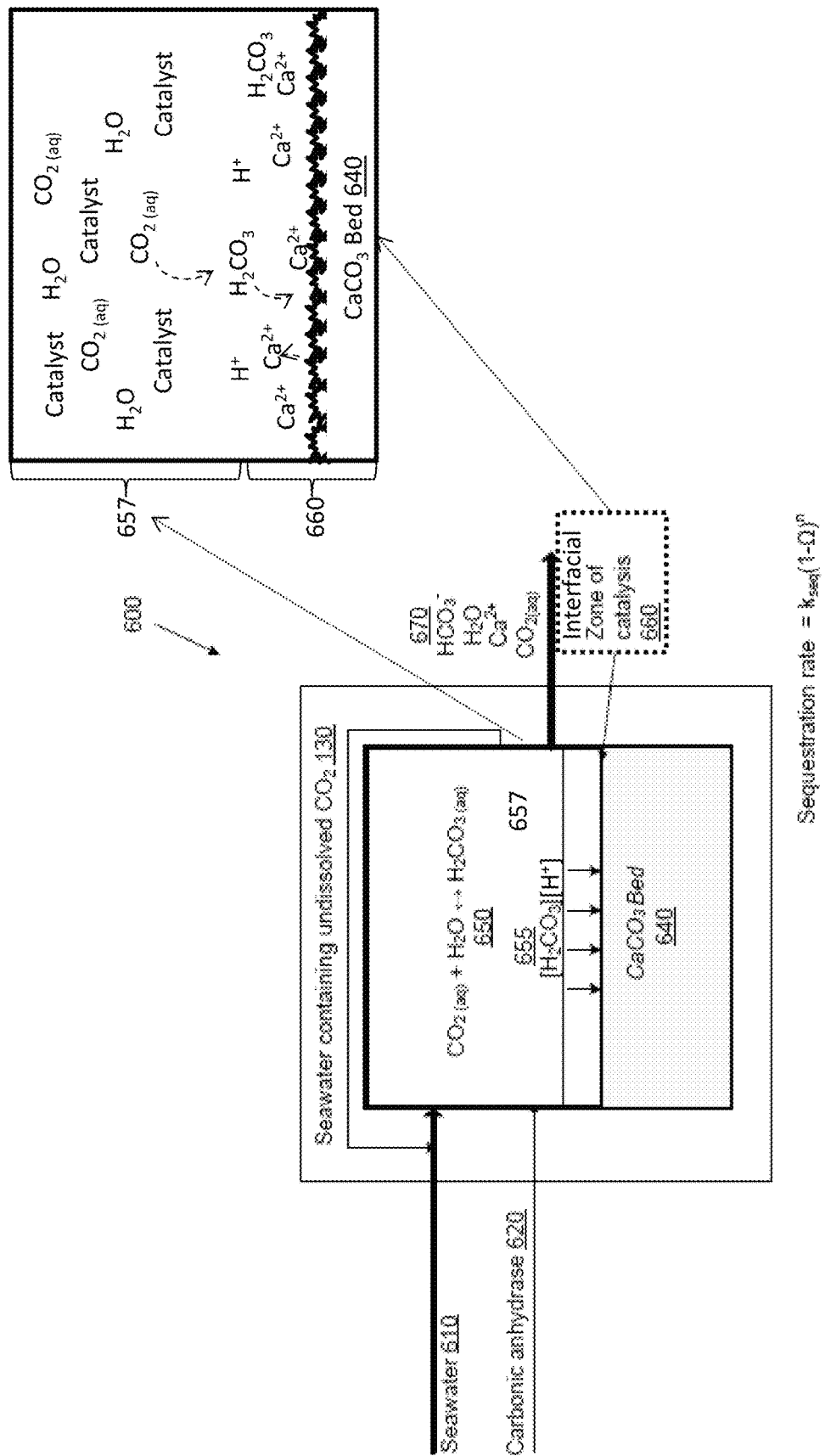
FIG. 2 provides a schematic flow chart of a carbon sequestration process in accordance with embodiments of the invention.

These principles are applied in an exemplary embodiment of a process (600), illustrated in FIG. 2 where the sequestration agent chosen is $CaCO_3$ (640). In FIG. 2, primary inputs into the system are seawater (610), a catalyst (620), and a sequestration agent (e.g., a metallic carbonate, such as calcium carbonate, 640), although it will be understood that in other embodiments additional inputs (as described above) including, for example, additives to decrease contaminants, temperature, pressure, etc. may be provided, as will be described in greater detail below. In the exemplary embodiment the seawater input 610 is premixed to contain aqueous $CO_2$. It should be understood that many mechanisms to improve the mixing of water and $CO_2$ to form an aqueous $CO_2$ are contemplated in embodiments. For example, the seawater may be aerosolized and/or agitation or other stirring mechanisms may be provided. In addition, the pressure and temperature of the reaction vessel may also be controlled as necessary to increase reaction rates. Likewise, although specific sequestration agents and catalysts are discussed in reference to FIG. 2, it will be understood that equivalent alternatives to these inputs may be chosen as will be discussed further below.

As previously discussed, due to the thermodynamics of hydration, seawater contains about one thousandth the amount of $H_2CO_3$ as $CO_{2(aq)}$. In embodiments of the process, a catalyst (e.g., carbonic anhydrase) is combined with the seawater in a first catalysis region (657) which surrounds a second interfacial catalysis region (660) that at least defines the interface between the solution in the first catalysis region (657) and the surface of a solid sequestration agent (in this example, carbonate) to form a controlled or engineered interfacial catalysis region (660). Within the first catalysis region (657), the combined seawater, catalyst (650) and sequestration agent act to increase replenishment of bulk protons (e.g., $[H^+]$ and $[H_2CO_3]$) (655) at the interfacial catalysis region sequestration agent above levels found in the absence of carbonic anhydrase, as discussed above in reference to the standard ratios of $H_2CO_3$ and $CO_{2(aq)}$ in uncatalyzed $H_2CO_3^*$. The first catalysis region is further engineered to deliver and replenish the concentration of protons within the second interfacial catalyzed region such that the rate of dissolution of the sequestration agent can be maximized independent of mineral undersaturation at or near equilibrium. In particular, in many embodiments it has been found that the addition of a suitable catalyst, such as, for example, carbonic anhydrase if delivered within a first catalysis region surrounding the second interfacial catalysis region (e.g., in some embodiments defined by the laminar boundary layer of the sequestration agent), can operate to equilibrate pools of $CO_{2(aq)}$ and protons (e.g., $H^+$ and $H_2CO_3$) and drive dissolution rates of the sequestration agent up to 3 orders of magnitude faster than natural thermodynamics and kinetics allow for a fixed level of mineral undersaturation. Accordingly, embodiments of apparatus and method provides systems for introducing a catalyst, such as, for example, carbonic anhydrase to a solution containing dissolved $CO_2$ in a controlled manner at the interfacial catalysis region (660) defined at the interface between the seawater solution and the $CaCO_3$ sequestration agent to greatly enhance the $CaCO_3$ dissolution kinetics ($k_{seq}$).

In accordance with embodiments, the formation of a controlled catalyzed region where relatively high concentrations of protons are present in close proximity to a sequestration agent (such as, for example, calcium carbonate) also decreases reactant transport time. Reactant transport is another slow step in the reaction process. By decreasing reactant transport through, for example, water protolysis and hydrating $CO_2$ in the presence of a sequestration agent, the two slow steps of the carbonate dissolution are decreased, and the reaction rate is greatly increased. Thus, in many embodiments the system and method requires the formation of an aqueous solution containing at least water and $CO_2$ and the controlled introduction of this aqueous $CO_2$ solution into a first engineered catalyzed region containing at least a catalyst suitable for catalyzing the production of protons from the protolysis of water and/or the hydration of aqueous $CO_2$ to carbonic acid. The first catalyzed region in turn encompasses a second interfacial catalyzed region proximal to a source of a suitable sequestration agent, such as, for example, a carbonate. By engineering the first catalyzed region and second catalyzed region such that the protons can be delivered between the regions (i.e., from the first catalyzed region to the second interfacial catalyzed region) a virtuous cycle of $CO_2$ hydration, carbonate dissolution and diffusion of these reactants together is formed (630).

Engineered $CO_2$ sequestration carried out as described provides for greatly enhanced sequestration rates not observed elsewhere or possible with other methodologies because the slow step of hydration is enhanced through catalysis and the requirements of reactant transport are also minimized by carrying out both reactions concurrently in the same vessel in a controlled manner within the catalyzed regions. In such embodiments the system output (670) is the product of the dissolution reaction, e.g., in the case of a $CaCO_3$ sequestration agent, calcium and bicarbonate ions ($Ca^{+2}$ and $HCO_3^-$).

Turning to the sequestration agent, in some embodiments the sequestration agent may be a mineral material such as for example, carbonates (e.g., metal carbonates), silicates, etc. Suitable calcium carbonates may include any number of such mineral carbonate species, such as, for example, calcite, aragonite, dolomite, vaterite, etc. In various embodiments, one or more such sequestering agents may be used in combination. Accordingly, many embodiments use metal carbonate sequestration agents, while some embodiments use non-carbonate sequestration agents such as for example silicate minerals, and in some further embodiments, sequestration agents include various mineral admixtures. Finally, in yet other embodiments, sequestration agents are a combination of carbonate and non-carbonate solids.

Figure 6:
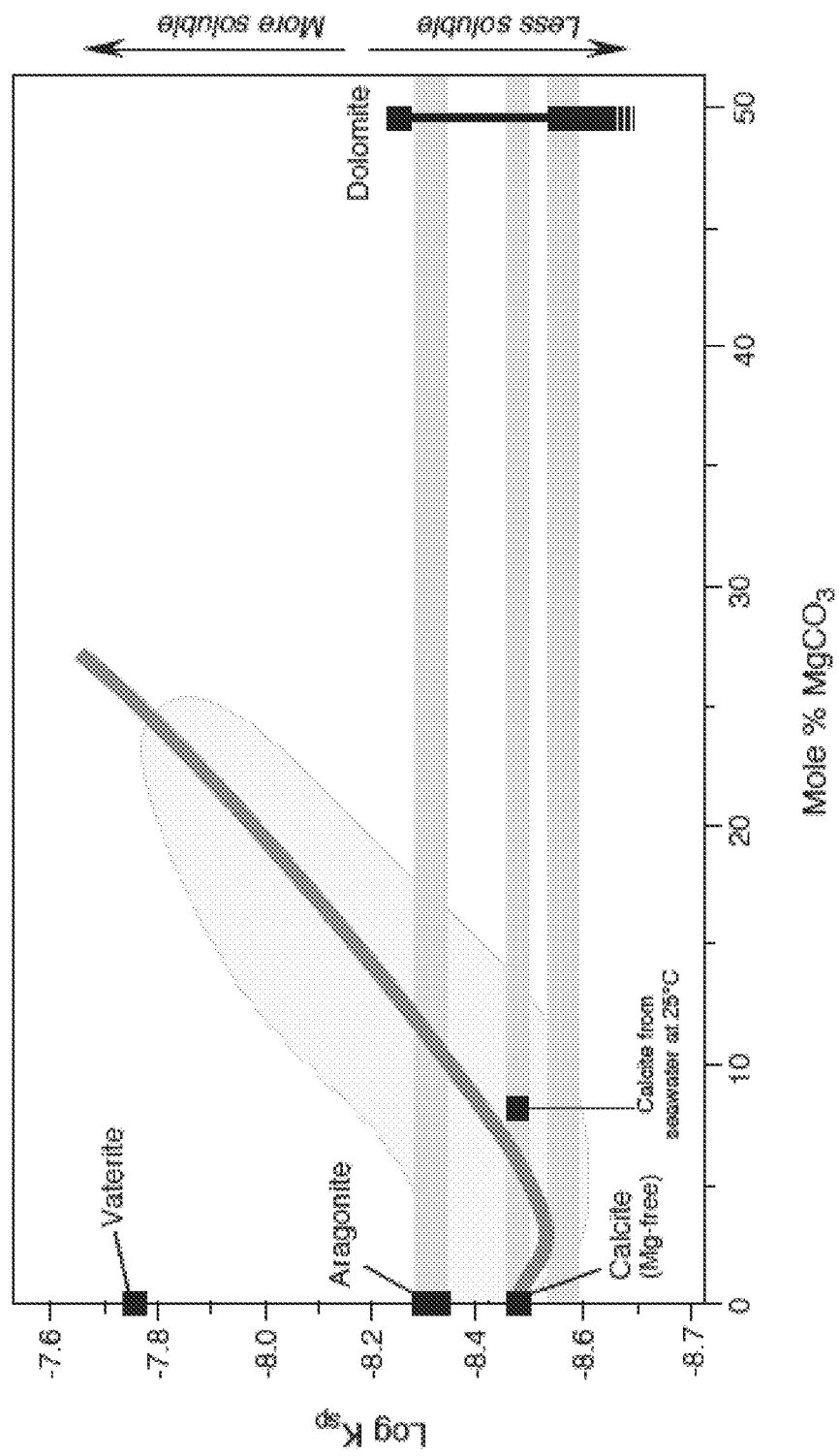
FIG. 6 provides a data graph plotting the solubility of carbonates versus Mole % of Mg.

Accordingly, although a calcium carbonate sequestration agent is discussed above, the choice of sequestration agent or agents may be made based on their solubility characteristics to allow for the further control of the sequestration potential of the controlled catalysis process and apparatus. More soluble minerals will leave a mixture with less mineral and higher carbonate ion concentration at equilibrium. In turn, a higher carbonate ion concentration is equivalent to a greater total neutralization, and thus greater potential $CO_2$ storage. As shown in FIG. 6, calcite is the least soluble mineral. Aragonite is more soluble than calcite by about a factor of two, and vaterite is even more soluble (i.e., by a factor of about five). Meanwhile dolomite spans a wide range of solubility, and can be much less soluble than calcite in some forms, while disordered dolomite is more soluble than both aragonite and calcite. As further shown in FIG. 6, magnesium has a strong influence on the solubility of calcium carbonate. Indeed, in the plot it can be observed that calcite solubility increases as Mg content increases. Accordingly, in other embodiments the Mg content of calcite can be tuned such that high-Mg content calcite can be used when a highly soluble mineral is to be used.

Further, as previously discussed, the sequestration agent, regardless of material, may be incorporated into the system in many different forms, but in some embodiments, it may be optimally formed to maximize surface area exposed to the seawater-catalyst solution. For example, it may be formed into 1 $mm^3$ cubes, or it may be crushed into smaller particles or shapes to maximize roughness to increase surface area. Alternatively, the sequestration agent may be incorporated into a large fluid path/high surface area fluidized bed reactor having baffles or waffles or other high surface area constructions. In general, greater sequestration agent surface area allows for greater reactant diffusion, more dissolution and therefore a higher rate of carbon sequestration, as will be understood by those skilled in the art.

In some embodiments, systems, methods and apparatus are provided in which the catalysis of the dissolution and sequestration are diffusion limited. In such embodiments, where the limit of catalysis to drive the reaction rate is reached, the only remaining limit on the capture and sequestration of carbon is in the ability of diffusion to deliver new reactants from the first catalysis region to the second interfacial catalysis region at the sequestration agent surface, which can be conceptualized as the diffusive reaction flux. A diffusive reaction flux can be calculated from the gradient of products and reactants across a boundary layer of known thickness, and is defined as:

$$\text{Flux} = D\frac{d[C]}{dx},$$

where d[C] is the difference in concentration of reaction products in the interfacial catalysis region near the sequestration agent surface (in this case presented as a carbonate) and in the bulk solution, dx is the thickness of the boundary layer, and D is the molecular diffusion coefficient of the carbonate ion. In some embodiments of this system, the term $d[C]=[CO_3^{2-}]_{sat}-[CO_3^{2-}]_{bulk}$, where $[CO_3^{2-}]_{sat}$ is the solubility product (divided by $[Ca^{+2}]$) at the mineral surface and $[CO_3^{2-}]_{bulk}$ is the concentration in bulk solution. A diffusive reaction boundary layer may act as a barrier for diffusive reaction flux. At reasonable stirring rates, the diffusive reaction boundary layer may be on the order of 10 microns. In embodiments of the invention reaching the diffusion limit, transport may be limited only by $d_x$, the thickness of the boundary layer.

In short, for a solid sequestration agent such as a carbonate mineral, the diffusion limitation is typically conceptualized as a reactant flux calculated for transport of products away from the mineral surface. In contrast, in embodiments of systems, methods and apparatus where the diffusion limit is reached, the reaction may be limited by transport of reactants to the mineral surface. Accordingly, in many embodiments methods and systems are provided to increase transport of reactants within the catalyzed region to the sequestration agent, to improve the ability of diffusion to deliver new reactants to the catalyst region (e.g., by creating the thinnest boundary layer possible between the first and second catalyzed regions and/or delivering the maximum amount of reactant from the first catalyzed region into the second interfacial catalyzed region).

Figure 7:
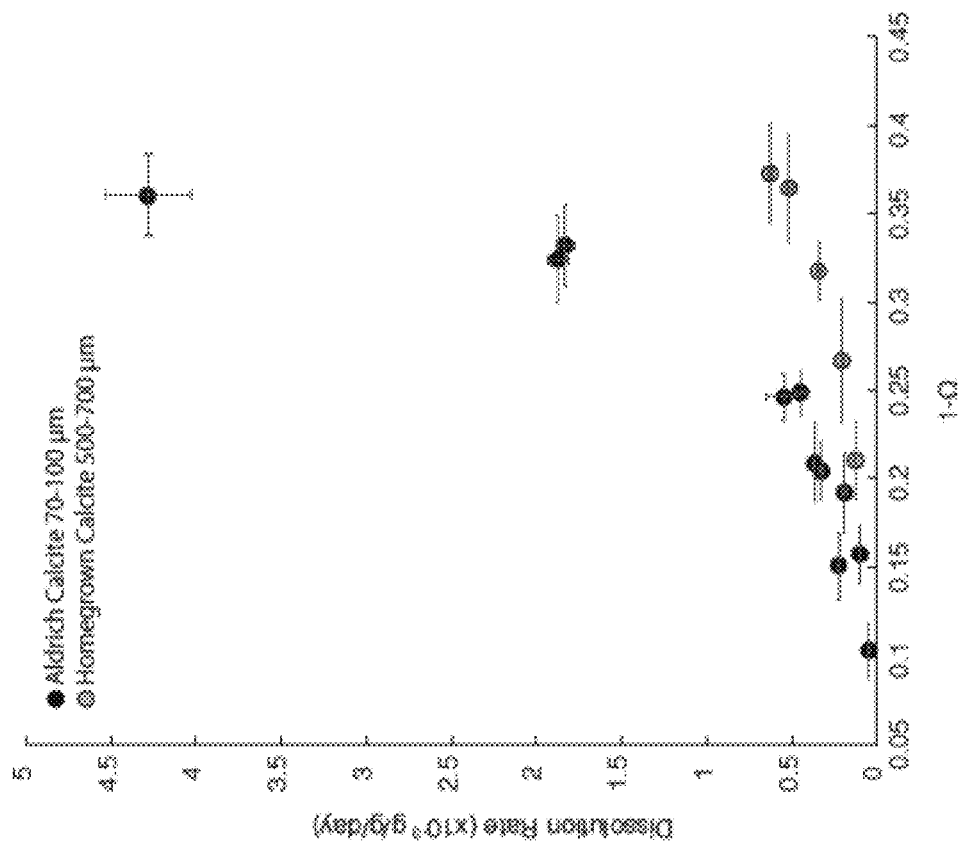
FIG. 7 provides a data graph plotting the calcite dissolution rates versus mineral undersaturation (1–Ω).

In additional embodiments, methods can be employed to produce the thinnest boundary layer possible between the first catalysis region and the interfacial catalysis region. Such method may include increasing the concentration gradient to deliver the maximum amount of the reactant to the interfacial catalysis region. Such methods may also include mixing or stirring the reactants, or placing the reactants and sequestration agent in proximity through a high-surface area construction such as a fluidized bed reactor. In embodiments, systems, methods, and apparatuses for carbon sequestration may further include varying the surface area and conformation of the sequestration agent. It has been shown that the surface area of the sequestration agent affects the rate at which dissolution and $CO_2$ neutralization will occur, as smaller grains have larger surface areas than larger grains per mass. FIG. 7 provides a data plot illustrating the relationship between grain size (in diameter, in μm) and dissolution rate for a given degree of mineral undersaturation (FIG. 7). The curves indicate that dissolution rate scales with grain size. Thus in various embodiments, smaller grain size may be desirable to drive dissolution. In some embodiments, considerations regarding grain size involve weighing several factors, including but not limited to the energy and cost of crushing the sequestration agent material for use in a reactor balanced with how rapidly that sized material will need to be replenished and how rapidly $CO_2$ sequestration can occur. In a variety of embodiments, particles of sequestration agent may be milli- or micrometer sized. Hence, material grain size is an adjustable and controllable parameter in driving $CO_2$ dissolution. The surface of the sequestration agent may also be roughened to increase the surface area of the interfacial catalysis region and thereby maximize exposure of the first catalysis region to the second interfacial catalysis region.

As discussed above, various non-carbonate sequestration agents may be used in systems, methods, and apparatuses for $CO_2$ sequestration with the addition of siderophore-like compounds or other catalytic compounds (such as carbonic anhydrase). In some embodiments, non-carbonate sequestration agents are silicate minerals. Weathering reactions on the earth's surface sequester $CO_2$ in the generalized reaction in which silicate minerals are altered to bicarbonate, a cation and dissolved silica.

$$2CO_2+3H_2O+CaSiO_3 \leftrightarrow 2HCO_3^-+Si(OH)_4$$

The incongruous weathering of Si-bearing minerals results in progressively slower dissolution kinetics with time in a reactor, however the agitation of reactor grains and rapid kinetics as catalytically enabled with the addition of siderophore-like compounds or other compounds (such as carbonic anhydrase) will enhance mineral dissolution and $CO_2$ sequestration. Accordingly, various mineral admixtures including non-carbonate minerals may be used in various embodiments.

Figure 8:
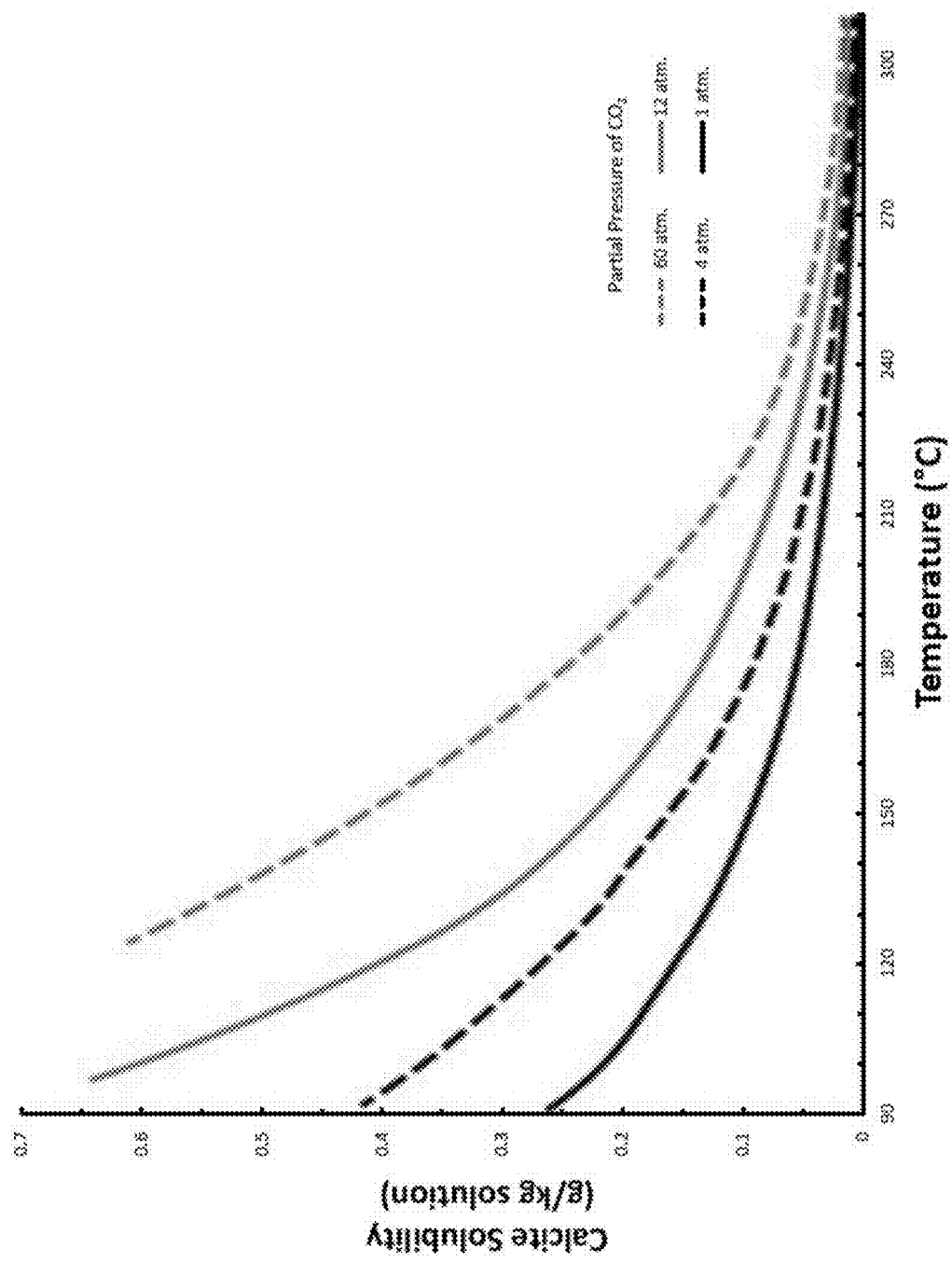
FIG. 8 provides a data graph adapted from Barnes (Barnes (ed.), Barnes (ed.), *Hydrothermal Ore Deposits*, (1997), the disclosure of which is incorporated herein by reference) plotting calcite solubility as a function of temperature and pressure of $CO_2$.

In systems, methods, and apparatuses for carbon sequestration, temperature control will depend on the desired kinetic and thermodynamic effects. For example, calcite becomes less thermodynamically soluble as temperature increases (FIG. 8), but more soluble as temperature increases due to kinetics. FIG. 8 depicts data plots illustrating calcite solubility as a function of temperature and pressure. In these plots, the curves demonstrate decreased solubility with increased temperature and increased solubility with increased pressure of $CO_2$ (FIG. 8). Accordingly, in certain embodiments, such as those using calcite as a sequestration agent, it may be necessary to balance thermodynamic and kinetic processes in determining the appropriate dissolution temperature. In view of these competing concerns, which may arise as a result of a chosen sequestration agent, temperature may optionally be determined based on either increased solubility to the detriment of dissolution rate or increased dissolution rate to the detriment of solubility.

Figure 9:
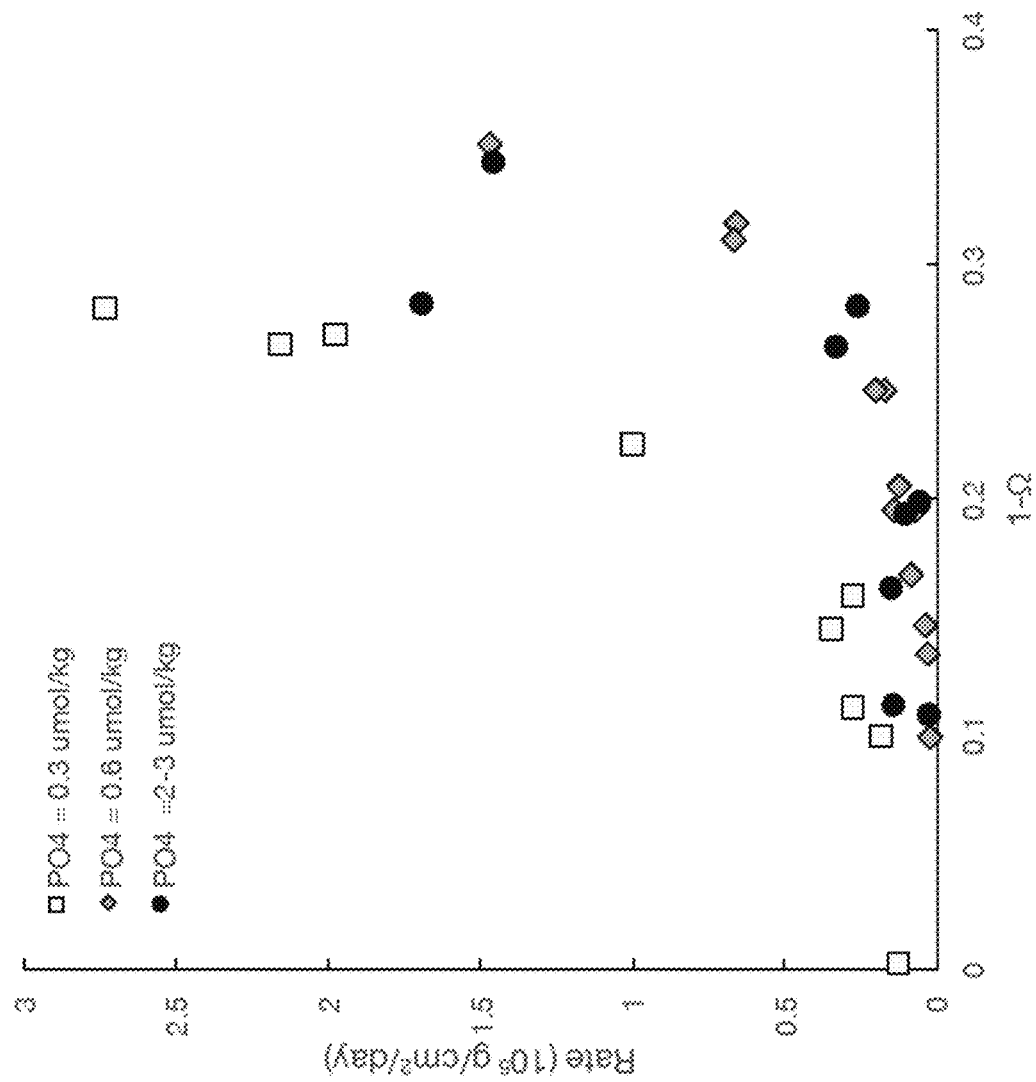
FIG. 9 provides a data graph plotting the dissolution rate of calcite as a function of saturation state and phosphate concentration.

In some embodiments of the invention, contact between the sequestration agent and surface poisoning ions is curtailed via the addition of condition agents. The inhibitory effect of surface ions like phosphate has been proven and is well known. For calcite, surface poisoning by phosphate ions is a function of at least: (1) the concentration of phosphate ion in the solution, and (2) the available surface area of calcite that phosphate can adsorb to. FIG. 9 illustrates the inhibitory effect of surface poisoning ions in comparing the dissolution rate of calcite as a function of saturation states and phosphate concentration. FIG. 9 indicates that, below a threshold (in some embodiments an undersaturation of 0.2 and in some cases 0.3), lowering the phosphate concentration increases the dissolution rate close to equilibrium. Thus, the data plot in FIG. 9 is at least also a function of the amount of calcite and the surface area of the available calcite, and demonstrates that lowering the amount of adsorbed inhibitor per square meter of calcite surface area increases the reaction rate. To enhance $CO_2$ sequestration, various embodiments of systems, methods, and apparatuses introduce conditioning agents to lower the amount of adsorbed inhibitor, or surface poisoning ions in contact with the sequestration agent surface(s).

Figures 10A, 10B:
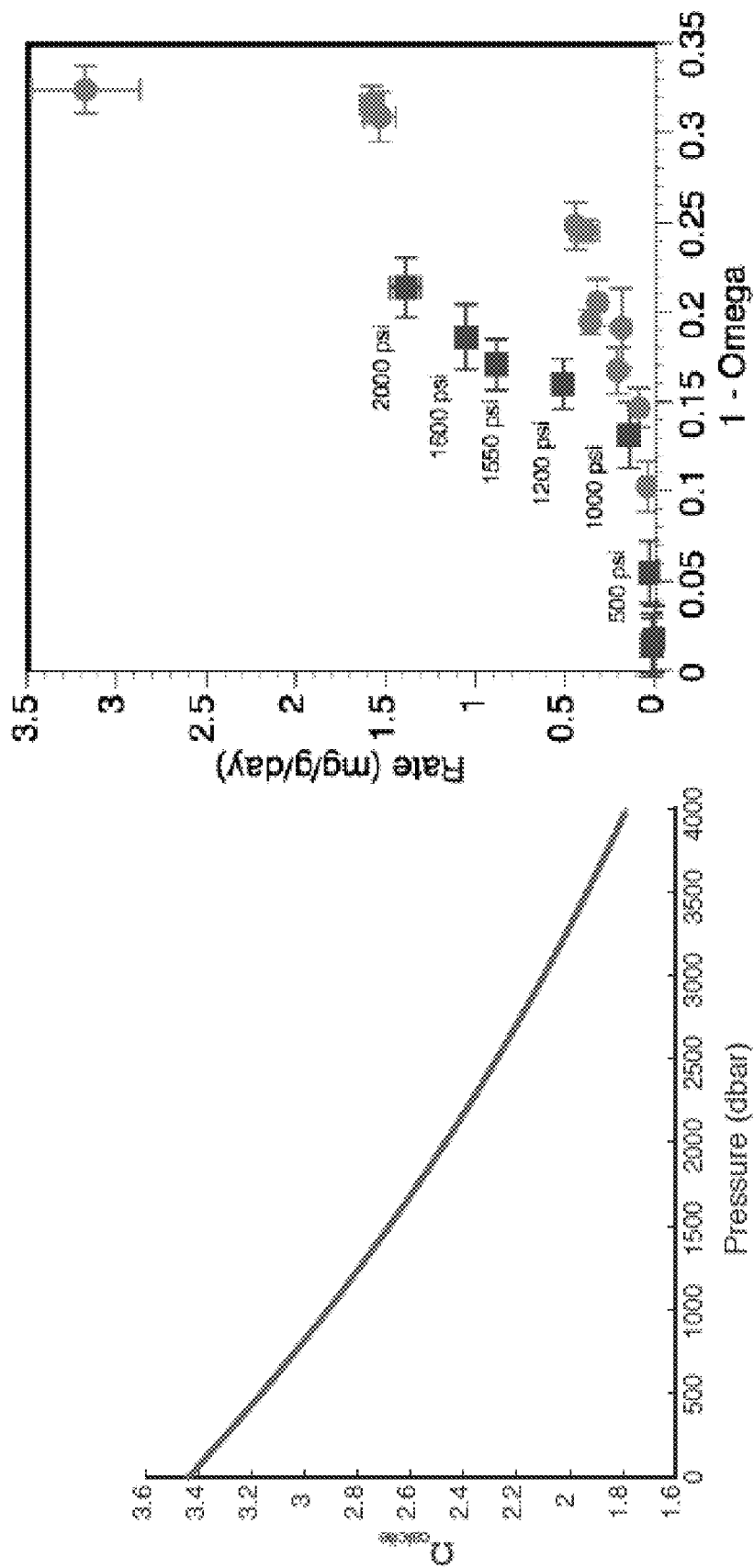
FIG. 10A provides a data graph plotting the effects of pressure on calcite saturation state.
FIG. 10B defines the effect of pressure on dissolution rate for a given degree of undersaturation.

Embodiments of the invention may also be controlled to operate at various pressures. In various embodiments, for many sequestration agents increases in pressure are proportionate to increases in solubility. For example, it is well known that pressure increases $CaCO_3$ solubility; an increase from ambient surface pressure to 400 bar increases solubility by a factor of two (FIG. 10) Under pressure, the kinetics of $CaCO_3$ dissolution is effectively greater for a given saturation state as compared to dissolution kinetics for the same mineral saturation state at ambient pressure (FIG. 10B). Thus, dissolution under pressure both drives a faster dissolution rate due to greater solubility (FIG. 10A) and also increases the kinetic (rate) of dissolution (FIG. 10B). Higher pressure scales to higher dissolution rate, with a greater effect farther from equilibrium. Accordingly, in some embodiments, rates of dissolution are controlled using pressure as one of the adjustable parameters. In many such embodiments, a pressure of at least 500 psi is used, in other embodiments at least 1000 psi, in still other embodiments at least 1500 psi, and in yet other embodiments at least 2000 psi.

Figure 11:
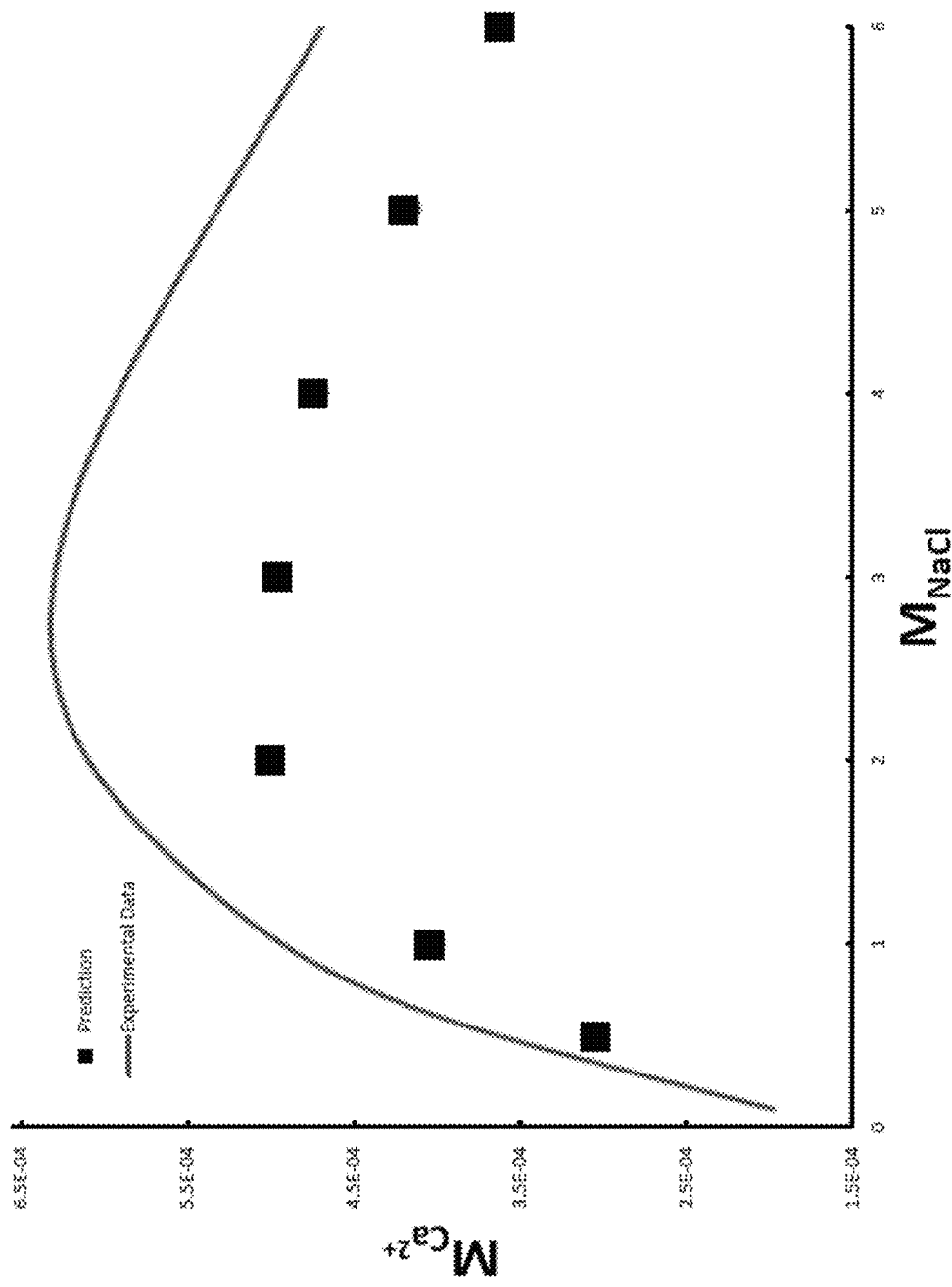
FIG. 11 provides a data graph adapted from Coto et al. (Coto et al. *Fluid Phase Equilibria* 324:1-7 (2012), the disclosure of which is incorporated herein by reference) plotting calcite solubility as a function of salinity.

Embodiments of the invention may use various aqueous solutions. Salinity of these solutions can affect the solubility of various sequestering agents. For example, the solubility of $CaCO_3$ is greater in salty water (given NaCl as the major salt in solution) compared to fresh water. In response to increased solution salt content, corresponding changes to solubility are non-linear and there is a maximum in solubility based on concentration of NaCl (FIG. 11). Thus, in some embodiments, the use of brine solutions may be used to yield faster dissolution than would occur in fresh waters. Accordingly, in some embodiments the concentration of NaCl is form at 1-6 M NaCl, in other embodiments from at 1-5 M NaCl, in still other embodiments from at 1-4 M NaCl, and in yet other embodiments from at 2-3 M NaCl.

Although the discussion to this point has focused on a carbonic anhydrase catalyst in various embodiments of carbon sequestration methods, one or more catalysts may be presented in a variety of forms sufficient to create a zone of catalysis. Accordingly, in many embodiments any catalyst suitable for: (1) increasing the protolysis of water to form $OH^-$ and $H^+$, and/or (2) increasing the local activity of hydroxide ion ($OH^-$), and/or (3) increasing the local activity of hydrogen ion ($H^+$) and/or, (4) increasing the physical separation between $OH^-$ and $H^+$, all without a change in the bulk pH of solution may be utilized. Exemplary embodiments of such catalysts may include, for example, carbonic anhydrase, carbonic anhydrase analogues and or materials with carbonic anhydrase active sites, and nickel, such as nickel nanoparticles, among others. In other embodiments the catalyst can be fixed to surfaces within a reactor vessel or fixed to surfaces which are then fed into a reactor vessel in some embodiments. In various embodiments, catalyst is dissolved. In further embodiments, dissolved catalyst in an effluent stream is recovered using enzyme separation techniques. In yet other embodiments, to separate enzyme, enzyme filtration is used. Enzyme filtration can be accomplished using any combination of polyethersulfones (PES), cellulose acetate (CA), sulfonated polyethersulfones (SPES), or polyvinylidene fluoride (PVDF) nanofiltration or ultrafiltration membranes using membrane layers, membrane pore, or hollow fibers. In further embodiments, membrane filtration is set up to periodically reverse flow direction relative to the filtration membrane or utilize non fouling membranes. Any combination of these techniques for providing and retaining catalyst can be used in additional techniques.

Although specific systems, methods, and processes for carbon sequestration by utilizing catalysis schemes in proximity to a sequestration agent are discussed above with respect to FIGS. 2 to 11, any of a variety of systems, methods, and/or processes for performing carbon sequestration utilizing a catalysis scheme in combination with a sequestration agent as appropriate to the requirements of a specific application can be utilized in accordance with embodiments of the invention. Thus, for example, in many embodiments a variety of reactants may be used, a variety of sequestration agents may be used, including but not limited to carbonate compounds, e.g. calcium carbonate, and non-carbonate compounds used alone or in combination. In other embodiments various catalysis schemes may be utilized to provide high concentrations of hydrated $CO_2$ in proximity with a sequestration agent. Additionally, the aqueous solution is not limited to seawater as described above, but may be briny or freshwater. In several embodiments, solutions may involve, but are not limited to, aqueous solutions of neutral, circum-neutral, or acidic pH. Furthermore, for several embodiments, it should be clear that $[CO_{2(aq)}]$ may vary. Although a single reaction is described in relation to the process and methods, in other embodiments, the method steps may be repeated such that seawater still containing undissolved $CO_2$ may be further hydrated to more thoroughly sequester the carbon. Embodiments, systems, methods and apparatuses for carbon sequestration may also involve the adjustment of several parameters. In embodiments, these parameters include at least the surface area, conformation, or type of sequestration agent, exposure of sequestration agent to surface poisoning ions, pressure, temperature, and salinity. Methods to tune the mineral undersaturation and diffusion coefficient may also include altering the temperature, pressure, and/or salinity within one or both of the catalyzed regions. Alternatively, the temperature and/or pressure of the system can also be controlled to increase dissolution of the saturation agent at a fixed mineral undersaturation.

Comparison With Conventional Sequestration Systems

Figure 12:
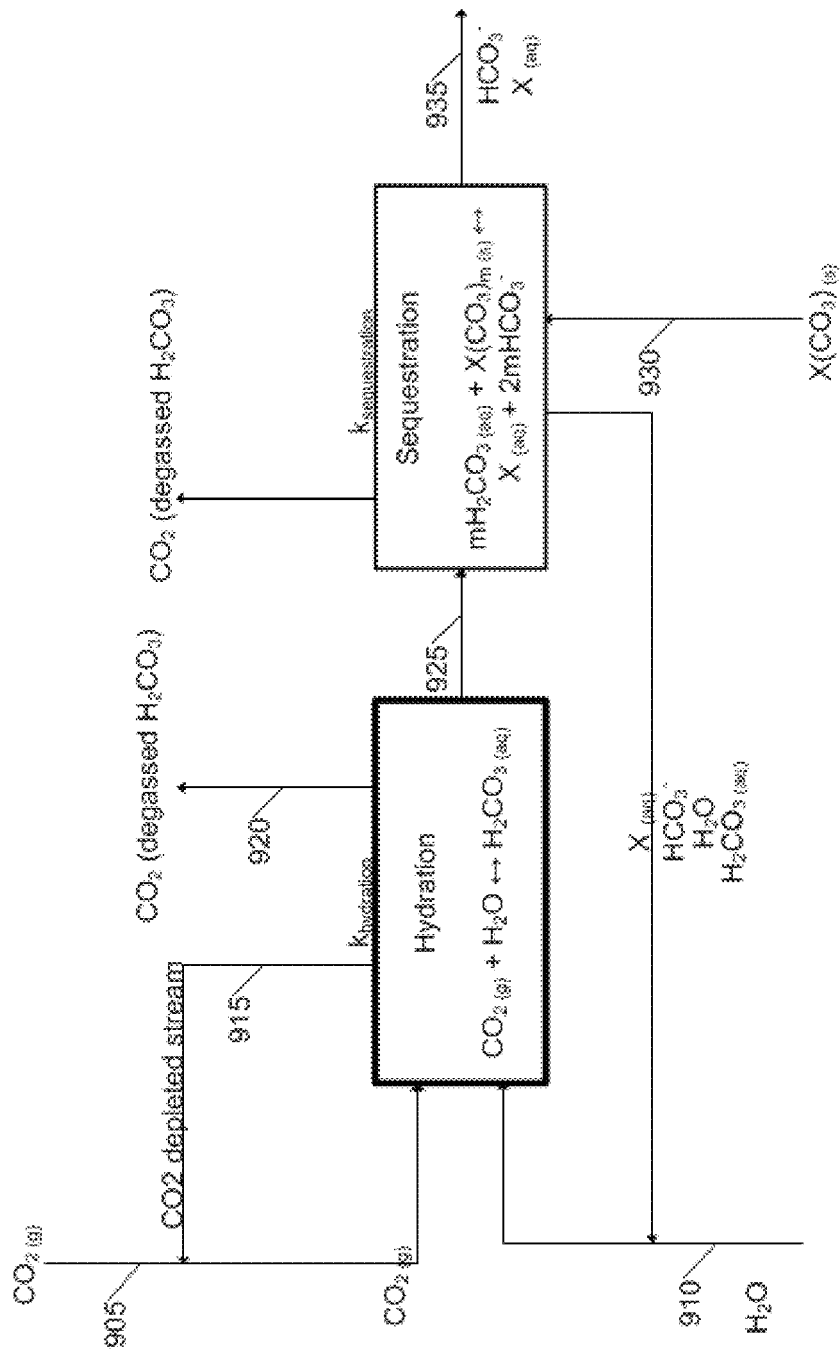
FIG. 12 provides a schematic flow chart of a carbon sequestration process in accordance with a conventional system.

Other sequestration strategies use carbonate dissolution, but these differ from the methods and embodiments described in some important aspects. Conventional $CO_2$ hydration systems typically describe a two-step process involving separate hydration and dissolution steps, as shown in FIG. 12. In the first step, hydration, inputs are gaseous $CO_2$ (905) and water (910) and outputs are a $CO_2$ depleted gas stream (915), $CO_{2(g)}$ liberated from a hydrated solution (degassed $H_2CO_3$ and $CO_2$) (920), and an aqueous solution containing a mixture $H_2CO_3^*$ (925) comprising $H_2CO_3$ and orders of magnitude greater amounts of $CO_{2(aq)}$. In the sequestration step, the solution containing $H_2CO_3^*$ (925) is reacted with a sequestration agent (930) such as a metal carbonate to yield a metal and bicarbonate product (930). In conventional systems one of the primary objectives of the first step (hydration) of this process is to increase the amount of $H_2CO_3^*$ in solution by dissolving high concentrations of $CO_2$ into solution, thus increasing carbonic acid in solution. In such systems it is generally preferable that the carbonic acid solution be as low in pH as allowed by the operating temperature, the incoming gas stream's $pCO_2$, the water volume with which $CO_2$ is hydrated, and the effects of chemical additives (if any). The $CO_2$ input, or gas stream, can be recirculated for further $CO_2$ removal. In the second step of the sequestration process, the carbonic acid is reacted with metal carbonate to yield a metal and bicarbonate product (930).

In these conventional methods of sequestration, emphasis is on the first step of the dissolution reaction—the hydration step. Such methods require that as much $CO_2$ as possible be dissolved into solution (to increase $CO_{2(aq)}$) to achieve the highest possible concentration of carbonic acid. However, a problem with this, and emphasis on increasing $H_2CO_3^*$ to sequester carbon in general, is that there are small amounts of $H_2CO_3$ relative to $CO_{2(aq)}$ in such solutions, and further there is a strong tendency for $CO_{2(aq)}$ to degas from solution.

In many embodiments of the systems, methods, and processes, these problems are resolved by a novel method of catalysis whereby a controlled catalyzed region rich in protons (e.g., $H^+$ and $H_2CO_3$ is formed in close proximity to the sequestration agent (e.g., carbonate minerals). As described above, such systems, methods, and processes obviate the potential problems associated with the transport of dissolved $CO_2$ and its degassing because large amounts of $CO_2$ are, not forced into solution to increase $H_2CO_3$* levels. As shown in FIGS. 2 to 11, for embodiments of the systems and methods utilizing the catalyzed carbonate reaction region, no additional $CO_2$ need be dissolved in circum-neutral pH solutions for seawater during hydration. Degassing is further minimized because reactant transport is minimal since within the catalyzed region the hydrated $CO_2$ reacts almost immediately with carbonate after the protons are formed. Accordingly, embodiments of systems and methods for carbon sequestration eliminate problems associated with $CO_2$ degassing by decreasing the need for high levels of gaseous $CO_2$, and also minimizing reactant transport. The result is a carbon sequestration method that operates at near equilibrium and is much faster than processes that require far from equilibrium mineral undersaturation to operate at comparable rates.

Catalyzed Sequestration Apparatus Embodiments

Figure 13A:
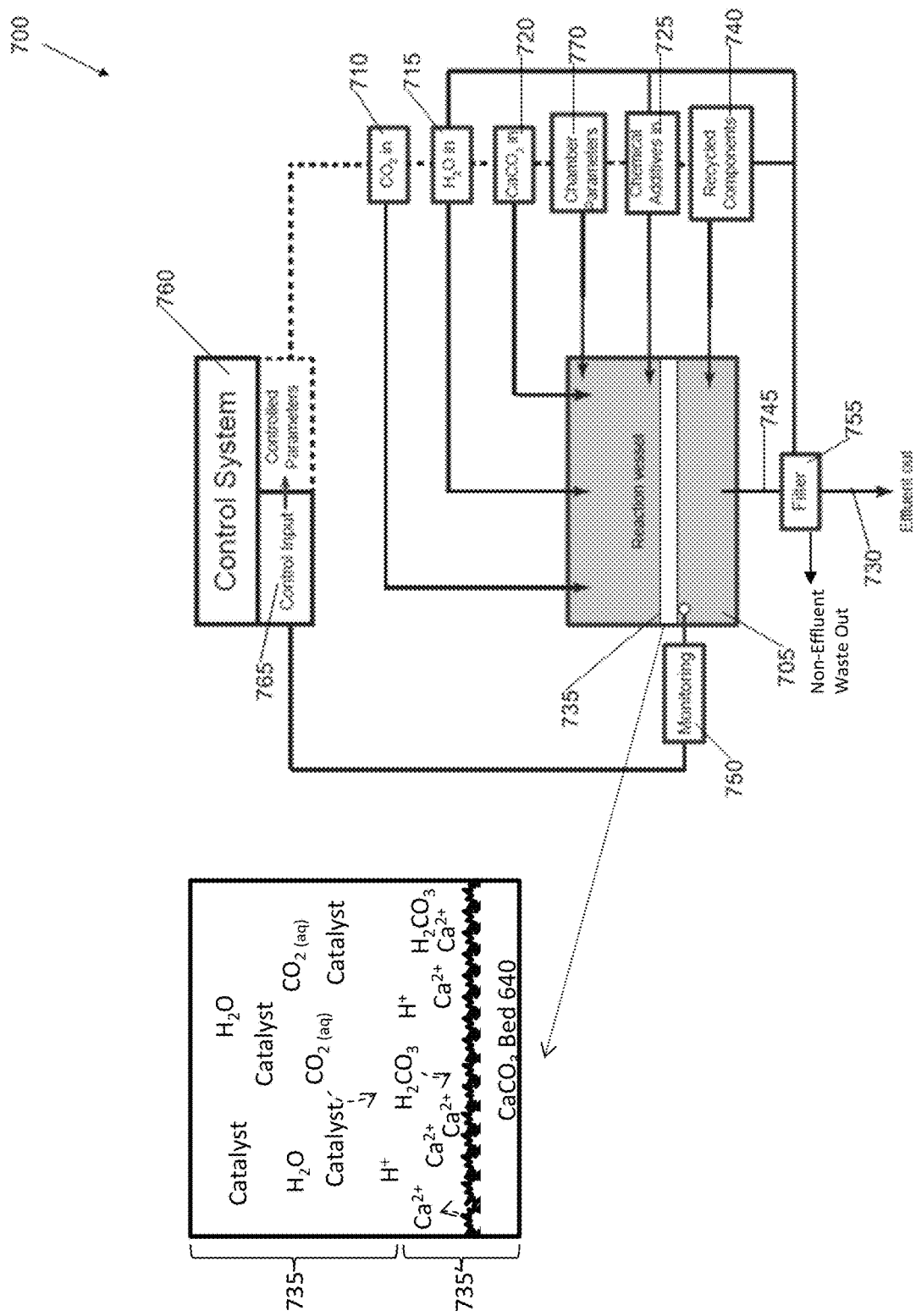
FIG. 13A provides a schematic of a one vessel carbon sequestration apparatus in accordance with embodiments of the invention.
Figure 13B:
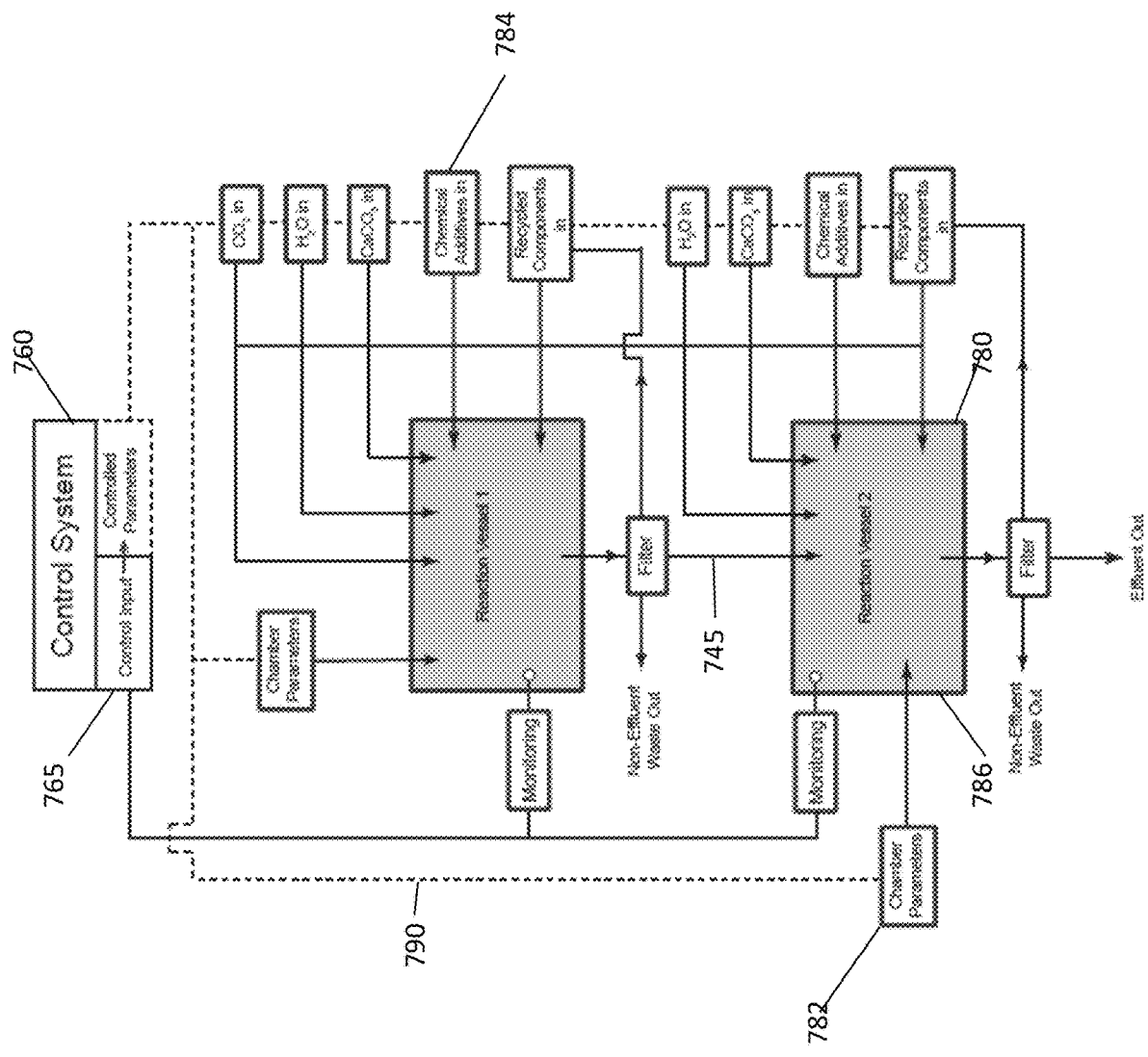
FIG. 13B provides a schematic of a two vessel carbon sequestration apparatus in accordance with embodiments of the invention.

Although systems and methods of carbon sequestration in accordance with embodiments have been described, it should be understood that apparatus embodying these novel systems and methods are also contemplated. FIGS. 13A and 13B provide exemplary sequestration systems as applied in many possible apparatus embodiments.

As shown in FIG. 13A, various embodiments of the invention can include (but are not limited to): a reactor vessel (705), a $CO_2$ input (710), an aqueous solution input (715), a sequestration agent input (720), a hydrating catalyst input (725) and/or a bicarbonate solution output stream (745), as illustrated in exemplary apparatus 700. In these embodiments, the various inputs, outputs and reactants are arranged such that at least the sequestration agent, catalyst and $CO_2$ solution are brought into reacting proximity to form two controlled catalysis regions (735 and 735') or zones within the reactant vessel.

In many embodiments, the first catalysis region (735) is formed in a region surrounding the sequestration agent where the $CO_{2(aq)}$ solution and catalyst are introduced together. This first catalysis region, in turn, encompasses a second interfacial catalysis region or zone formed around at least the interfacial region of the sequestration agent (e.g., at the laminar boundary layer of the sequestration agent) such that a catalytic cycle is formed whereby the rate of proton replenishment from ($CO_2$ hydration and water hydrolysis) in solution at the interfacial region are enhanced. In some embodiments the interfacial catalysis region is defined as the volume within the reaction vessel at least within the diffusive reaction boundary layer of the sequestration agent. In other embodiments, the interfacial catalysis region may be defined by the laminar boundary layer of the sequestration agent, thereby allowing for an increase in the concentration of protons in the solution bulk, which can serve to increase the dissolution of the sequestration agent (e.g., carbonate ion) at mineral undersaturations near or at equilibrium. In many embodiments, the apparatus produces a sequestration agent dissolution rate within the controlled catalysis region greater than the sequestration agent dissolution rate of an uncatalyzed system at the same solution undersaturation. In many embodiments, the apparatus produces a sequestration agent dissolution rate within the controlled catalysis region at least one order of magnitude greater than the sequestration agent dissolution rate of an uncatalyzed system at the same mineral undersaturation. In other embodiments, the sequestration agent dissolution rate within the controlled catalysis region is at least two orders of magnitude greater than the sequestration agent dissolution rate of an uncatalyzed system at the same mineral undersaturation. In still other embodiments, the sequestration agent dissolution rate within the controlled catalysis region is at least three orders of magnitude greater than the sequestration agent dissolution rate of an uncatalyzed system at the same mineral undersaturation.

In many embodiments, input feed streams flow into the reactor at various points and flow out of the reactor at various points such that the catalysis regions are formed and preserved throughout the sequestration process. Still, in other embodiments, the input and output streams may be calibrated to operate at steady state. In yet other embodiments, the feed streams do not operate at steady state. In other embodiments the catalysis zones are formed and preserved by separate structures within the reaction vessel that defined the controlled catalysis zones (e.g., permeable vessels within the larger reactor vessel, fluidized beds, flow paths, waffle or baffle constructions, etc).

In some embodiments, the reactor vessel has sufficient volume such that the first catalysis region forms about a second interfacial catalysis region at the $CO_{2(aq)}$ solution-sequestration agent interface (e.g., at the laminar boundary layer of the sequestration agent). Catalyst may be added at various points in the reactor to enhance the formation of the catalysis zone at the $CO_{2(aq)}$ solution-sequestration agent interface. In additional embodiments, the reactor may be of a size and/or volume such that a mixing zone forms wherein various inputs may themselves mix together and additionally mix with the sequestering agent. It will be understood that such a mixing region may or may not extend outside the first and/or second catalysis zone such that reactants are carried into at least the first and/or second catalysis zone for sequestration as a result of the mixing. Additionally, the reactor may be of any size deemed sufficient by one skilled in the art to accommodate reactor inputs, sequestration agent, and reactor outputs. Various embodiments of the invention involve a reactor vessel of a shape determined by one skilled in the art to be suitable for the described embodiments of the invention.

In some embodiments, the reactor vessel will have at least one input, which may involve a mixture comprising at least $CO_2$, aqueous solution, and/or catalyst, and at least one output, which involves at least a bicarbonate-enriched solution.

Various embodiments of the invention will have different configurations of input streams, such that the flows combine in the reactor to yield controlled regions of catalysis. In FIG. 13A, the embodiments of the exemplary apparatus 700 shown have at least five input streams, involving (but not limited to): $CO_2$ (710), $H_2O$ (715), $CaCO_3$ (720), chemical additives (i.e., catalyst and anti-poisoning materials), and recycled components (740). Calcium carbonate ($CaCO_3$) (720) is used as a sequestration agent in the embodiments described, but it will be understood that other sequestration agents may be substituted. Furthermore, chemical additives are described as at least a catalyst, such as carbonic anhydrase, but one skilled in the art will recognize that other catalysts may be substituted. Thus, embodiments of the invention may have unique inputs for each reactant feed stream, i.e., separate streams for $CO_2$, aqueous solution, catalyst, and sequestration agent. Alternatively, in other embodiments, it will be understood that there may be fewer input streams, particularly where multiple reactants are combined into a single stream. For example, $CO_2$ and aqueous solution may be combined into a single stream, and this may be also further combined with sequestration agent. A second input stream may contain catalyst. The two streams can be combined in a reactor such that the two catalysis regions form about the solution-sequestration agent interface. One skilled in the art will recognize that one, two, or three input streams may be used and that in various reactants may be combined into single input streams.

The location of input and output streams may be at various locations in the reactor. Reactants and catalyst may flow into the reactor through inputs located at points to at least partially ensure the formation of first catalysis zone encompassing a second interfacial catalysis region at the interfacial region around the sequestration agent. Outputs (745) may be located at points on the reactor to remove bicarbonate product while maintaining the presence of the catalysis regions (735) surrounding the sequestration agent.

Inside the reactor, inputs may be combined in a variety of ways to facilitate the formation of the catalysis regions, as described above. As is shown in the exemplary embodiment described in FIG. 13A, inputs including (but not limited to) $CO_2$ (710), aqueous solution (715), chemical additives, including catalyst (725), and/or sequestration agent (720) may be combined in a reactor mixing zone, resulting in the formation of a first region of catalysis (735) and a second interfacial catalysis region (735') surrounded by the first catalysis region and disposed at the interface of the sequestration agent ($CaCO_3$) bed. According to embodiments, sequestration agent may be present in various conformations, i.e. millimeter scale particles, to increase catalysis zone surface area. In a variety of embodiments, $CO_2$ may be combined with at least aqueous solution inside the reactor. For example, in some embodiments the catalysis region (735) may be formed, for example, as a separate permeable vessel within the larger reactor vessel (705). In such an embodiment the catalysis region may have inlets along its surface sized such that the catalyst and sequestration agent materials are confined therein, but wherein the other elements in the reaction (e.g., aqueous solution and $CO_2$) are allowed to freely intermingle therewith or are move therethrough in a pressurized stream thus creating and enforcing the first and second catalysis regions.

In the reactor, in addition to catalysis (discussed in more detail below) $CO_2$ hydration may be enhanced by techniques involving (but not limited to): increasing the surface area of the aqueous solution in contact with a given volume of gaseous $CO_2$ and/or bubbling, increasing the $pCO_2$ of the income gas stream, increasing pressure of the $CO_2$ gas stream and increasing $CO_2$ solubility by decreasing temperature. In other embodiments, $CO_2$ and aqueous solution may be combined prior to reaching the reactor. For example, $CO_{2(aq)}$ may already be present in some solutions, i.e. seawater, or it may be mixed in a mixing vessel prior to entering the reactor vessel.

The reactor may be maintained at various pressures to modify the dissolution rate of the sequestration agent in accordance with embodiments of this invention as set forth as determined by one with skill in the art. In some embodiments, reactor pressure may be increased by the injection of gas (for example, $CO_2$) under pressure or injection of solution (for example, water) under pressure. In further embodiments, pressure is released through check valves. In yet other embodiments, pressure is released by regulating the outflow pressure relative to the inflow pressure.

Catalyst can be added in quantities sufficient such that a first catalysis zone forms to encompass a second interfacial catalysis region at the interface of the sequestration agent and solution. The concentration of catalyst in such embodiments can be tuned to one or both: 1) maximize the replenishment of bound protons from $H_2CO_3$ produced from the $CO_{2(aq)}$ reservoir of the reaction vessel; and 2) maximize the production of free protons from the protolysis of water. In some embodiments, the solution may be mixed over a bed of sequestration agent, and/or with particles of sequestration agent to increase surface area and reduce the boundary layer between the first and second catalysis regions. Where the diffusion limit is reached, catalyst may be added such that there is a standing stock of carbonic acid in the first catalysis region such that a maximum amount of reactant is delivered into the second interfacial catalysis region.

The sequestration agent used in the reactor may involve a variety of physical conformations. To enhance sequestration, various embodiments may utilize conformations of sequestration agent that have increased surface area. In some embodiments, considerations regarding grain size involve weighing several factors, including but not limited to the energy and cost of crushing sequestration agent for use in a reactor balanced with knowledge of how rapidly that sized material will need to be replenished and how rapidly $CO_2$ sequestration can occur. In a variety of embodiments, particles of sequestration agent may be milli- or micrometer sized.

Particles may be fed into the reactor as needed. Or alternatively, in other embodiments particles may be replaced in batches. In yet other embodiments, sequestration agent may exist as a bed within the reactor. A zone of catalysis can form over the surface of the bed, as catalyst and $CO_{2(aq)}$ solution are distributed over it. Sequestration agent material may be of varying sizes and roughness to enhance surface area. Alternatively, the sequestration agent may be incorporated into a large fluid path/high surface area fluidized bed reactor having baffles or waffles or other high surface area constructions.

The reactor may be maintained at a temperature deemed by one skilled in the art appropriate for the sequestration process to proceed and dissolution rate and diffusion coefficients of the sequestration agent to be optimized.

Fresh or saline water containing $CO_2$ may be fed into the reactor. In some embodiments, the water is freshwater. In many embodiments inlet water is seawater, or another saline solution. In some embodiments a brine solution will yield greater rates of dissolution.

The reactor may also be maintained at neutral, circumneutral, or acidic pH, or at pH levels such that the sequestration process proceeds in accordance with embodiments of this invention as set forth as determined by one with skill in the art. In other embodiments, the reactor may involve a stirrer to decrease the boundary layer surrounding sequestering agent materials, particularly when the sequestration rate reaches the diffusion limit.

In many embodiments, the reactor may have monitors (750) at various points to monitor various parameters, including reactant, catalyst, pressure, salinity, surface poisoning ions, product, pH, and temperature. In various embodiments, monitors may be located at various input and output streams at points where the stream flows into the reactor. Other embodiments may involve monitors located inside the reactor. More specifically, monitors inside the reactor may be placed to detect and measure zones of catalysis and sequestration.

In various embodiments of the invention, input streams feed at least one stream of $CO_2$, aqueous solution, and catalyst into the reactor. In some embodiments, an additional sequestration agent feed may replace depleted sequestration agent inside the reactor vessel. In other embodiments, the sequestration agent may be replenished to the reactor in batches. Input streams may comprise combinations of reactants that are combined prior to reaching the reactor. Various embodiments can involve for example (but are not limited to) one input stream comprising at least $CO_2$, aqueous solution, and sequestration agent combined and an additional input stream comprising at least catalyst sufficient to ensure the formation of a zone of catalytic activity. Some embodiments may additionally include a mixing vessel to combine input streams before they reach the reactor. For example, this mixing vessel may dissolve gaseous $CO_2$ into aqueous solution before addition of the catalyst. Additionally, sequestration agent may be fed into the reactor in a separate stream. Some of these mixed-input streams may comprise components recycled from effluent streams including at least one of aqueous solution, sequestration agent and catalyst (740).

In some embodiments of the invention, outputs (745) of the reactor may include at least a bicarbonate-enriched solution. Additionally, outputs may involve (but are not limited to): excess aqueous solution, $CO_2$, catalyst and/or sequestration agent. In many embodiments, outputs may leave the reactor in at least one stream, so long as there is a zone of catalysis at the interfacial region between the solution and the sequestration agent. Additionally, in various embodiments, outputs may leave the reactor at various points, such that the zone of catalysis remains at the interfacial region is maintained. Placement and/or flow of output streams may also be designed to ensure that the zone of catalysis remains at the interfacial region is maintained. The above variables may also be optimized to maximize the zone of catalysis.

Optionally, some embodiments may have a filter (755), from which various components of the output stream (745) can be extracted, retained, or recycled, resulting in an effluent stream (730).

Figure 14:
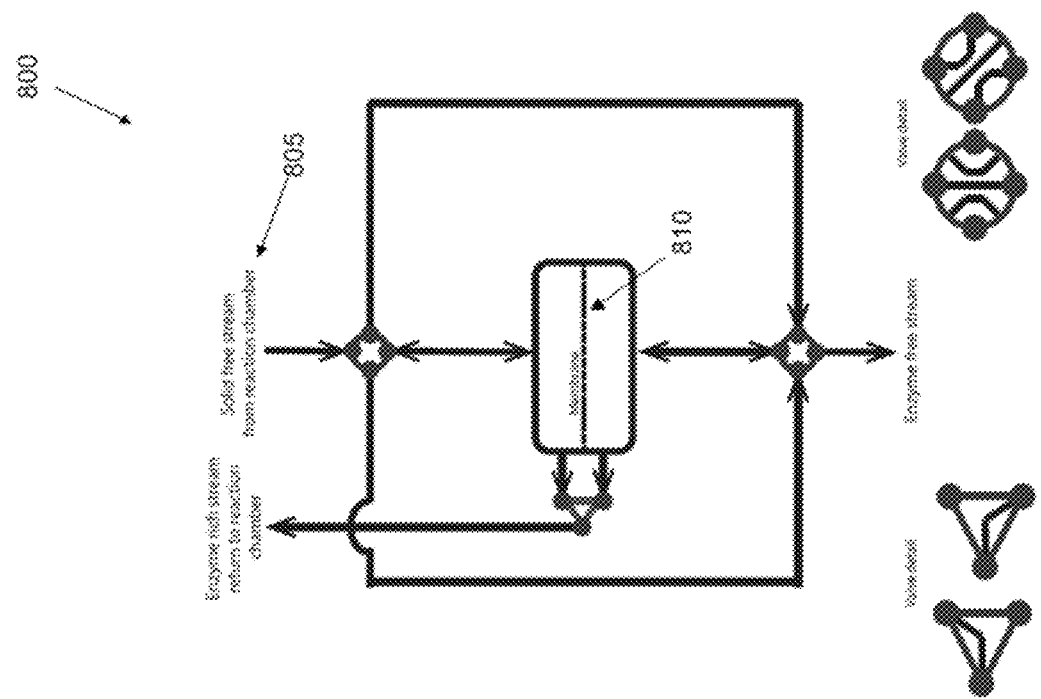
FIG. 14 provides a schematic diagram of an enzyme separation filter for use in a process for carbon sequestration in accordance with embodiments of the invention.

Many embodiments employ various mechanisms for retaining sequestration agent at the reaction site (755) (FIG. 13A). In some embodiments, effluent water is filtered using a particle filtration system (FIG. 14). In additional embodiments, a settling chamber is optionally added where reactant can settle to the bottom and effluent, solid-free water can be sipped or discharged off the top of the chamber. The settling chamber can be the main reaction vessel or a secondary reaction chamber. In yet other embodiments, a combination of mechanism for retaining sequestration agent may be used.

Optionally, some embodiments may have one or more reactors, which are fed from a first reactor, to hydrate and sequester any $CO_{2(aq)}$ remaining in solution. As an illustration of an exemplary embodiment, FIG. 13B shows a second reactor (780) located downstream from the first reactor with inputs that may primarily include outputs (745) from the first reactor, particularly aqueous solution and undissolved $CO_2$ with catalyst. This primary flow leaving the first reactor feeds a second reactor, which is parameterized separately (782) in order to completely neutralize or degas any residual $CO_2$. In other embodiments, additional inputs to the second reactor may include catalyst (784), i.e., carbonic anhydrase as shown in FIG. 13B or other catalysts recognized as appropriate by one having skill in the art. In other embodiments, sequestration agent may be present in batches, e.g., a carbonate bed (786) as shown in FIG. 13B, or sequestration agent may be replenished in a steady state or as deemed necessary through optional monitoring. In many embodiments, the secondary reaction taking place in the second reactor may provide a $CO_2$—neutral, alkaline solution as effluent. The resulting effluent can be mixed with ambient environmental fluids, such as seawater. In some embodiments employing a two-stage reactor where the sequestration agent is retrograde soluble, the temperature may be high in a first stage and lowered in a second stage such that the first reactor has the fastest dissolution rate, but the second reactor increases the total amount of carbonate dissolved over a longer time. In embodiments using such two vessel arrangements one or both of the first or second vessels may include the two-catalysis region constructs described above. The size of the two reactors may vary according to the desired reaction time.

In many embodiments of an apparatus, the apparatus controls and continually adjusts mineral undersaturation in the reactor device using a feedback loop (790). In a feedback loop, a control system may monitor and adjust, for example, the input of various parameters, particularly catalyst and $CO_2$ into the reactor at circum-neutral pH (between 6.5 and 7), as shown in FIGS. 13A & 13B. In some embodiments, the control system operates to ensure that the apparatus operates at the maximum, catalyzed dissolution rate, neutralizing as much $CO_2$ as possible per unit reaction time. In a variety of embodiments, the control system may process monitored input parameters and may adjust other process parameters appropriately.

In many embodiments, the control system (760) monitors the process from various monitoring points. Some embodiments of the invention may involve monitors at various points in the reactor apparatus. Monitors may detect parameters (765) including but not limited to pH, temperature, pressure, salinity, surface poisoning ions, $pCO_2$, $TCO_2$, flow rate, and/or reactant input, including sequestration agent, and catalyst input. Various embodiments have monitors inside the reactor (770). Inside the reactor, monitors may in some instances be located at input and/or output streams. Alternatively, monitors may also be placed near the catalytic zone (e.g., within the interfacial region of the sequestration agent).

In various embodiments, catalyst retention strategies may be employed such that catalyst is appropriately provided in the carbon sequestration process and retained. Retention of catalyst minimizes potential environmental impact and reduces catalyst cost. Reactor embodiments utilize various methods of catalyst retention (FIG. 14). In some reactor embodiments, catalyst is fixed to the surface of free-floating solids (i.e., beads) surface, and these solids are retained using the same methods as for the retention of reactant materials (805). In yet some more embodiments, catalyst is fixed to surfaces within the reactor vessel. Surfaces to which catalyst can be fixed includes but are not limited to reactor walls, membranes, rods, sheets, or any object that can be fixed into the reactor chamber. In additional embodiments, dissolved catalyst can be separated from a solid-free effluent stream and retained using an enzyme separation technique and returning the catalyst rich stream to the reaction vessel. For enzyme filtration, any combination of PES, CA, SPES, PVDF or equivalent nanofiltration or ultrafiltration membranes (810) using membrane layers, membrane pores, or hollow fibers may be employed. In various embodiments, membrane filtration is set up to periodically reverse flow direction relative to the filtration membrane or utilize non-fouling membranes. In additional embodiments, catalyst may be replenished using an organism that expresses carbonic anhydrase. Additionally, a variety of valves may be used to control the rate and direction of output and effluent flow. Additional other embodiments use engineer organisms to produce catalyst. Organisms can be located within or outside the reaction vessel. In some embodiments, catalyst retention strategies can be combined.

In short, several embodiments of the invention involve a reactor within which $CO_2$, aqueous solution, sequestration agent, and catalyst are combined such that a first controlled catalysis region is formed to encompass a second interfacial catalysis region proximal (e.g., a the laminar boundary layer) of the surface of the sequestration agent to enhance rates of carbonate sequestration. One skilled in the art will recognize that the illustration is not a complete description of the invention and that inputs and outputs may be combined in a variety of ways in the second reactor to create such a catalysis zone.

Data Collection

The following provides information about the methods used to conduct the exemplary studies that produced the data provided in FIG. 3 showing the unexpectedly improved sequestration rates obtained using systems and processes in accordance with embodiments. It will be understood that this data and the accompanying examples are only provided as illustration and are not meant to limit the scope of the systems, methods and apparatus described throughout the disclosure.

Methods and Materials

In the observations provided with this disclosure in relation to FIG. 3 particularly, high precision stable isotope measurements, ubiquitous geochemistry, and chemical oceanography were used. The experiment methodology exploits the stable isotope of carbon $^{13}C$ as a direct tracer of mass transfer from mineral to solution. In general, calcium carbonates enriched in $^{13}C$ are placed in a closed system of undersaturated seawater. Then, the evolving $\delta^{13}C$ of this seawater is measured over time by discrete sampling, thus obtaining curves of moles dissolved over time.

Calcium carbonates enriched in $^{13}C$, while rather inexpensive and plentiful, are not ideal due to its sintered nature. A well-formed material that could be manipulated as an inorganic solid in a range of grain sizes is needed. To this end, calcium carbonates were grown in the laboratory, using a gel-diffusion method first described by Nickl, H. J., Henisch, H. K, 1969. *Journal of the Electrochemical Society Solid State Science* 116 (9), 1258-1260, the disclosure of which is incorporated herein by reference. In this method, a glass U-shaped tube is filled with 50 mL hydrous gel (in this case, pH-adjusted sodium metasilicate (0.17 M), separating 30 mL reservoirs of $CaCl_2$ and $Na_2^{13}CO_3$ (both 0.15 M) in each arm of the tube. The ends of the tube are sealed using Parafilm and rubber stoppers. In the process, nucleation of calcium carbonate crystals is limited by diffusion and the gel pore spacing, allowing for slow growth of large grains. The grains are harvested after 3-6 months of reaction time by pouring off the spent reservoir solutions followed by physical break-up, sonication, and decantation of the less dense gel matrix from the calcium carbonate grains. The grains are then triply washed in DDW and dried at 60° C. In this study, data is presented from gel-grown calcite, dry-sieved to several size fractions. The degree of isotopic labeling is measured using the Picarro CRDS on small (0.2 mg) aliquots of material, pre-acidified, and measured using the AutoMate Liaison autosampler.

The carbonate saturation state was constrained using dissolved inorganic carbon and alkalinity pairs. All experiments were performed in a Dickson seawater reference material (poisoned with mercuric chloride). Seawater aliquots of 2-3 L are transferred via siphon to 5 L Supelco gastight foil bags. Mineral undersaturation is achieved by titrating alkalinity via injection of HCl (0.1 M) through the sampling port septum of the foil bag. Thus, no DIC is lost during alkalinity titration. DIC does change slightly, but only due to dilution by the added HCl solution.

Alkalinity, determined by open-system Gran titration, is performed on a custom-built instrument. A Metrohm electrode connected to a Mettler Toledo SevenCompact pH meter was used. The titrant (0.05-0.1 M HCl in natural seawater medium) is delivered by a Metrohm 876 Dosimat Plus titrator with a 5 mL burette. A filtered 16 mL seawater sample is placed in a 25° C. water bath. The sample is stirred and bubbled with air throughout the measurement. The titration program controls the titration from a Windows laptop. Alkalinity is determined using a nonlinear least-squares approach as outlined in the Best Practices Guide (Dickson et al., *Pices Special Publication* 3, IOCCP Report No. 8. (2007)_, the disclosure of which is incorporated herein by reference). Dickson standard reference materials, as well as an in-house seawater alkalinity standard, are run at the beginning and end of every session to ensure analytical consistency and to monitor acid and electrode drift. Long-term alkalinity precision is about 2.5 μeq/kg. Long-term accuracy is about the same as precision; thus total alkalinity error over the long-term should be on the order of 3 μmol/kg.

Dissolved Inorganic Carbon (DIC) and seawater $\delta^{13}C$ are determined using a modified Picarro cavity ring down spectrometer with an AutoMate Liaison autosampler. About 7 mL of filtered seawater is injected into an evacuated 10 mL AutoMate vial from a syringe through the rubber septum screw-cap. The net sample weight is taken. The AutoMate acidifies these samples on-line using 10% phosphoric acid, and the resulting $CO_2$ is carried in a nitrogen stream, through a Nafion desolvating line, to the Picarro Liaison sampling bags. The flow rate is set to 80±0.2 cubic centimeters per minute (ccm) by a mass flow controller in between the autosampler and the Picarro. Drift in both DIC and $\delta^{13}C$ are monitored over the course of the run, and also over longer time periods. DIC values are corrected to reference material values, and samples are both blank-and standard-corrected. Since there are no available seawater $\delta^{13}C$ reference materials, $\delta^{13}C$ values are also normalized to a value of 1‰ (VPDB). Samples are corrected for instrumental drift using linear interpolation between bracketing standards (at the beginning, middle and end of the run). Also, a negative correlation between water content and [$^{12}CO_2$] was documented. Water content in samples was monitored, and a water correction was made as necessary as well. Drift is almost never above a few tenths of a permil, and resulting Picarro standards typically have a standard deviation of under 0.1‰. Replicate DIC and Alk analyses were taken advantage of, and standard errors were used when calculating experimental $\Omega$.

Alkalinity and DIC pairs are then converted to saturation state using CO2SYS run through MATLAB. The errors in Alkalinity and DIC are propagated to $\Omega_{calcite}$ by a monte carlo approach: Alk-DIC pairs are sampled randomly from normal distributions with their associated standard errors as the standard deviations, and the resulting $\Omega$ values are averaged. Errors on $\Omega$, calculated this way, are between 0.01 and 0.04 units. Carbonic acid dissociation constants are taken from the Dickson and Millero (Dickson & Millero. *Deep-Sea Research* 34, 1733-43 (1987), the disclosure of which is incorporated herein by reference) refit of Mehrbach's data (Mehrbach, et al. *Limnology and Oceanography* 18, 897-907 (1973), the disclosure of which is incorporated herein by reference). The calcite solubility data from Mucci (Mucci, *Am. J. Sci.* 09; 283(7) (1983), the disclosure of which is incorporated herein by reference) are used for calculation of $\Omega$ in CO2SYS.

All dissolution rate data presented were obtained on the benchtop at ambient temperature (20-22° C.). Several different materials for experiments were evaluated, since excellent control on saturation state was needed.

Experiments were performed in Supelco inert foil bags, which are stable for DIC and do not bleed or remove alkalinity, and polycarbonate sampling ports were fabricated. These ports have a built-in filter housing, such that sampled water is filtered through Nucleopore membrane filters (~0.2 μm). The port is fitted onto the bag through a punched hole, hand-tightened, and sealed with a Viton o-ring. Using this setup, both alkalinity and DIC blank experiments show no change over days to week.

Data is obtained in the following way: Supelco bags are cut open, and the sampling ports are fitted through the foil. Labeled material (3-5 mg) is weighed out and poured into the foil bag. The open bag is then heat-sealed twice. These bags are then evacuated to remove all headspace. Undersaturated fill water is then siphoned from its large foil reservoir into these experimental bags. First, about 50 grams is siphoned in, and grains are agitated and rinsed. This water is then removed through the sampling port via syringe and discarded. Then, about 300 grams of fill water is siphoned in, the bag is weighed to obtain the exact mass of water added, and the experiment is considered started. Once the experiment has started, bags are placed on a shaker table at 60 rpm. The shaking rate has been tested and it was found that at speeds above 60 rpm, the dissolution rate is the same as the rate at 60 rpm. Below 60 rpm, rates slow significantly, presumably due to stagnation and the formation of boundary layers around the grains. At each sampling point, the experimental bags are weighed. Samples are taken through the sampling port via a tygon tube attached to a plastic syringe. The syringe is washed with about 2 mL of the sampled water, and then a full 7 mL sample is taken. This sample is injected through a 0.45 μm filter into a pre-evacuated AutoMate vial for Picarro analysis, as described above. Initially, sampling occurs 2 or 3 times daily. As the experiment proceeds, however, sampling becomes more infrequent. Total experiment duration is 3-10 days. Since DIC and $\delta^{13}$ are measured simultaneously, DIC is monitored over the course of the run. Post-experiment alkalinity measurements are taken to check for alkalinity consistency.

Carbonic anhydrase solutions are prepared by dissolving carbonic anhydrase powder (Sigma Aldrich, CAS 9001-03-0) into deionized water and making serial dilutions. At high concentration (1 mg/mL), carbonic anhydrase solutions resemble those of soap, with a viscous surface and bubbles. Dissolution experiments are prepared as described above using 70-100 μm Aldrich 13C-labeled calcite. Just before the first time point is taken, a carbonic anhydrase solution is added to the experimental bag via syringe through the sampling port. The bag is then mixed well and the first time point is taken.

Effluent Characterization and Environmental Impact

A $CO_2$ neutralizing scheme will fail unless the reactant solution is abundant and leaves the scheme with no environmentally untenable impact. The systems, methods and apparatus detailed in the figures are based on a sequestration agent, such as carbonate solid reacting with $CO_2$ in a seawater medium, but could be applied with freshwater. The environmental implications of both scenarios are discussed below. In all cases the systems provided according to embodiments provide apparatus and processes that produce an outflow effluent having a lower partial pressure of $CO_2$ than the partial pressure of $CO_2$ provided in the in-flow to the system.

Many power plants use seawater as a coolant in a single pass or recycling mode. For example, withdrawal of seawater to cool a nuclear plant in the UK occurs at a rate of $8 \cdot 10^{15}$ L/day. If there were 1000 sequestration reactors as described in the embodiments, each operating so as to neutralize a proportionate daily $CO_2$ emission, then each reactor would need to dissolve $2.5 \cdot 10^{11}$ g of $CaCO_3$ per day. Assuming ocean surface waters have an alkalinity of 2100 μeq/L, the reaction of $CaCO_3$ described above would add alkalinity so as to increase ambient water alkalinities by 0.03%, a very small increase. Cooling water flow at a much lower rate would likely enhance alkalinity by only a few percent in the effluent. As these calculations demonstrate, a very small fraction of the cooling water may be shunted to a carbonate reactor site and returned to the effluent flow with minimal impact on effluent water quality.

Returning water to the surface ocean with slightly enhanced alkalinity is likely considered a trivial and non-threatening environmental outcome. For example, the upwelling rate of 3 m/day can occur in coastal regions for several months and over vast areas encompassing thousands of km of shoreline. Estimated coastal upwelling occurs at a rate of 1 Sv ($1 \cdot 10^6$ m³/sec=$8.6 \cdot 10^{13}$ L/day) per 1000 km of shoreline. Upwelling off coastal California adds alkalinity to the surface of the ocean at a rate of $3 \cdot 10^5$ μeq alkalinity/day (assuming 100 m water alkalinity of 2120 μM and surface alkalinity=2085 μM, Berelson, unpublished data). Embodiments of some reactors (assuming there are 1000 reactors) would only add $5 \times 10^{12}$ peq alkalinity/day to coastal ocean. The neutralization of a day's worth of global $CO_2$ emission, reacted with $CaCO_3$ and dumped in the coastal ocean would add alkalinity to the ocean in an amount equivalent to the amount of alkalinity added during upwelling along 1000 km of coastline. In other words, the coastal ocean, along only 1000 km, upwells more alkalinity to the surface ocean in one day than one giant reactor plant could add to the ocean in one day. Based on estimates, there may need to be about 3 reactors per 1000 km of coastline, which is still over 2 orders of magnitude below the natural flux of alkalinity from deep waters. Furthermore, the addition of alkalinity enriched waters to some coastal environments may be seem as environmentally favorable insofar as coastal environments are increasingly subjected to corrosive and environmentally harmful "acidified" waters (Feely et al., Global Biogeochemical Cycles 26 (3) (2012), the disclosure of which is incorporated herein by reference). There are documented impacts on coastal aquaculture that the addition of alkaline waters could mitigate.

A freshwater reactor is also feasibly operational and the effluent discharge alkalinity would be controlled by the flow rate and reaction rate for dissolution. Creating alkaline freshwater could be environmentally and economically favorable for several applications. Alkaline drinking water is marketed as a healthy alternative to standard drinking water. The product of carbonate dissolution and $CO_2$ sequestration could be a marketable and economically useful consumable. Another important application of alkaline freshwater is for agricultural purposes. Highly acidic soils, such as those in portions of the Northeast and Carolinas are not favorable for certain vegetables (asparagus, broccoli, beets, cabbage, carrots, cauliflower, lettuce, onions, peas, peppers, and spinach). Thus, the use of irrigation water with some alkalinity would be preferable treatment or amendment to acidic soils. Coupling a $CO_2$ sequestration plant to a farming irrigation system would yield a doubly beneficial outcome.

DOCTRINE OF EQUIVALENTS

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for carbon dioxide sequestration comprising:
dissolving carbon dioxide into an aqueous solution to form an aqueous carbon dioxide solution defined by a mineral undersaturation level;
combining the aqueous carbon dioxide solution with a sequestration agent;
titrating a hydrating catalyst into the aqueous carbon dioxide solution such that at least within a first catalysis region a mixture of catalyst and aqueous carbon dioxide solution is formed, said first catalysis region encompassing a second interfacial catalysis region located within the laminar boundary layer at the interface between the mixture and the carbonate sequestration agent; and
reacting the aqueous carbon dioxide solution with the catalyst within the first catalysis region to produce protons in proximity to the second interfacial catalysis region such that the protons dissolve the sequestration agent;
reacting the carbon dioxide within the aqueous carbon dioxide solution with the dissolved sequestration agent within the second interfacial catalysis region to produce an effluent comprising at least bicarbonate; and
wherein within the second interfacial catalysis region the dissolution of the sequestration agent is enhanced such that the overall rate of dissolution of the sequestration agent within the catalytic region is higher than the rate of the uncatalyzed dissolution of the sequestration agent when exposed to an aqueous carbon dioxide solution having the same mineral undersaturation level.

2. The method of claim 1, wherein the sequestration agent is selected from the group consisting of a metal carbonate, or a silicate mineral.

3. The method of claim 1, wherein the sequestration agent is calcium carbonate and the catalyst is one of either carbonic anhydrase or a carbonic anhydrase analog.

4. The method of claim 1, wherein the overall rate of dissolution of the carbonate sequestration agent is at least an order of magnitude higher than the rate of the uncatalyzed dissolution of the carbonate sequestration agent when exposed to an aqueous carbon dioxide solution having the same mineral undersaturation level.

5. The method of claim 1, wherein the mineral undersaturation level is held at less than 0.5.

6. The method of claim 1, further comprising placing at least the first catalysis region and the second interfacial catalysis region under a pressure of at least 500 psi such that the dissolution of the sequestration agent is increased relative to the unpressurized dissolution rate of the sequestration agent at the same mineral undersaturation.

7. The method of claim 1, further comprising maintaining at least the second interfacial catalysis region at a temperature no greater than 200° C.

8. The method of claim 1, further comprising reacting with a condition agent the aqueous solution to reduce surface poisoning ions in the aqueous carbon dioxide solution.

9. The method of claim 1, wherein the aqueous solution has a circum-neutral pH.

10. The method of claim 1, wherein the aqueous solution is a brine solution.

11. The method of claim 1, wherein the aqueous carbon dioxide solution is combined in measured aliquots such that the mineral undersaturation level is maintained at a constant level.

12. The method of claim 1, further comprising stirring the aqueous solution within at least the first catalysis region such that a mixing zone forms wherein the aqueous carbon dioxide solution and catalyst intermingle and wherein the mixing zone is within the first catalysis region.

13. The method of claim 12, wherein the stirring forms a diffusion boundary layer around the second interfacial catalysis region the diffusion boundary defining a volume around the interfacial region of the sequestration agent on the order of 10 microns.

14. The method of claim 1, further comprising roughening the surface of the sequestration agent such that the grain size of the sequestration agent is no greater than 100 μm.

15. The method of claim 1, further comprising collecting and filtering the effluent from the reaction to capture at least one of catalyst or unreacted aqueous carbon dioxide solution; and
reintroducing the catalyst and unreacted aqueous carbon dioxide solution into the first catalysis region.

16. The method of claim 1, wherein the catalyst operates to at least catalyze the protolysis of water in the aqueous solution and hydrate the $CO_2$ within the solution.

17. The method of claim 1, wherein the rate of dissolution is diffusion rate limited.

18. The method of claim 1, wherein at least one of either the pressure is increased or the temperature is decreased to increase mineral undersaturation.

19. An apparatus for sequestering carbon dioxide, comprising:
at least one reactor vessel defining an enclosed volume;
at least one source of a catalyst, a sequestration agent, a $CO_2$ gas, and an aqueous solution;
at least one input in fluid communication between the at least one source and the enclosed volume of the at least one reactor vessel; and
at least one output in fluid communication with the enclosed volume of the at least one reactor vessel;
wherein the at least one input is arranged such that the $CO_2$ gas and aqueous solution combine to form an aqueous carbon dioxide solution, and wherein the aqueous carbon dioxide solution and catalyst are delivered as a mixture within the enclosed volume of the at least one reactor within a first catalytic region encompassing a second interfacial catalytic region disposed about the sequestration agent and being located within a laminar flow boundary at the interface between the mixture and the carbonate sequestration agent.

20. The apparatus of claim 19, wherein at least one of the sequestration agent and catalyst is physically confined within the first catalytic region.

* * * * *